(12) United States Patent
Rocke et al.

(10) Patent No.: US 7,062,384 B2
(45) Date of Patent: Jun. 13, 2006

(54) METHODS FOR CLASSIFYING HIGH-DIMENSIONAL BIOLOGICAL DATA

(75) Inventors: David M. Rocke, Davis, CA (US); Danh V. Nguyen, College Station, TX (US)

(73) Assignee: The Regents of the University of California, Oakland, CA (US)

( * ) Notice: Subject to any disclaimer, the term of this patent is extended or adjusted under 35 U.S.C. 154(b) by 505 days.

(21) Appl. No.: 09/957,100

(22) Filed: Sep. 19, 2001

(65) Prior Publication Data

US 2002/0111742 A1 Aug. 15, 2002

Related U.S. Application Data

(60) Provisional application No. 60/233,546, filed on Sep. 19, 2000.

(51) Int. Cl.
*G06F 17/00* (2006.01)

(52) U.S. Cl. .................................................... 702/19

(58) Field of Classification Search ................ 702/19, 702/181, 196; 706/20; 382/133, 224; 700/91
See application file for complete search history.

(56) References Cited

U.S. PATENT DOCUMENTS

| | | | |
|---|---|---|---|
| 5,612,540 A * | 3/1997 | Richards-Kortum et al. ..... | 250/461.2 |
| 5,987,390 A | 11/1999 | Ladunga ....................... | 702/19 |
| 6,025,128 A | 2/2000 | Veltri et al. ..................... | 435/6 |
| 6,059,724 A * | 5/2000 | Campell et al. ............. | 600/300 |
| 6,203,987 B1 * | 3/2001 | Friend et al. .................. | 435/6 |

FOREIGN PATENT DOCUMENTS

WO WO 96/42070 12/1996

OTHER PUBLICATIONS

Hampel et al. Fast inversion scheme for the linearized problem in optical absorption tomography on objects with radially symmetric boundaries. Proceedings of the SPIE-The International Society for Optical Engineering. (1996) vol. 2925, pp. 31-42.*

Nguyen et al. Tumor classification by partial least squares using microarray gene expression data. Bioinformatics. (2002) vol. 18, No. 1, pp. 39-50.*

Romualdi et al. Pattern recognition in gene expression profiling using DNA array: a comparative study of different statistical methods applied to cancer classification. Human Molecualr Genetics. (2003) vol. 12, No. 8, pp. 823-836.*

Yeh et al. Partial least squares and classification and regression trees. Chemometrics and Intelligent Laboratory Systems. (1994) vol. 22, No. 1, pp. 17-23.*

Alaiya et al. Classifiaction of human ovarian tumors using multivariate data analysis of polypeptide expression patterns. Int. J. Cancer (Jun. 1, 2000) vol. 86, pp. 731-736.*

Golub et al. Molecular classification of cancer: class discovery and class prediction by gene expression monitoring. Science (Oct. 15, 1999) vol. 286, pp. 531-537.*

Bennett, K.P., et al., "Robust Linear Programming Discrimination of Two Linearly Inseparable Sets," Optimization Methods and Software, (1992) vol. 1, 23-24.

International Search Report, mailed Mar. 27, 2002, Corresponding PCT/US01/29731.

Kooperberg, C., et al., "Polychotomous Regression," Journal of the American Statistical Association, (1997) 92:437, 177-127.

Nakai, et al., "Cluster Analysis of Amino Acid Induces for Prediction of Protein Structure and Function," Protein Engineering, (1988) 2:2, pp. 93-100.

Tomi, K., et al., "Analysis of Amino Acid Indices and Mutation Matrices for Sequence Comparison and Structure Predictionof Proteins," Protein Engineering (1996) 9:1, pp. 27-36.

International Preliminary Examination Report, Application No. PCT/US01/29731, 6 pages, mailed Oct. 14, 2003.

* cited by examiner

*Primary Examiner*—Marjorie A. Moran
(74) *Attorney, Agent, or Firm*—Fenwick & West LLP

(57) ABSTRACT

Provided are methods of classifying biological samples based on high dimensional data obtained from the samples. The methods are especially useful for prediction of a class to which the sample belongs under circumstances in which the data are statistically under-determined. The advent of microarray technologies which provide the ability to measure en masse many different variables (such as gene expression) at once has resulted in the generation of high dimensional data sets, the analysis of which benefits from the methods of the present invention. High dimensional data is data in which the number of variables, p, exceeds the number of independent observations (e.g. samples), N, made. The invention relies on a dimension reduction step followed by a logistic determination step. The methods of the invention are applicable for binary (i.e. univariate) classification and multi-class (i.e. multivariate) classifications. Also provided are data selection techniques that can be used in accordance with the methods of the invention.

18 Claims, 5 Drawing Sheets

Original Gene Expression Matrix

PLS

Gene Component Expression Matrix

METHODS FOR CLASSIFYING HIGH-DIMENSIONAL BIOLOGICAL DATA

CROSS-REFERENCE TO RELATED APPLICATIONS

This application claims the benefit of U.S. Provisional Patent Application No. 60/233,546, filed Sep. 19, 2000, the contents of which are hereby incorporated by reference for all purposes.

STATEMENT REGARDING FEDERALLY SPONSORED RESEARCH

The U.S. Government has certain rights to the invention pursuant to contracts ACI 96-19020 and DMS 98-70172 awarded by the National Science Foundation and contract P43 ES04699 awarded by the National Institute of Environmental Health Sciences, National Institutes of Health.

REFERENCE TO A MICROFICHE APPENDIX

Not applicable.

BACKGROUND OF THE INVENTION

The invention pertains to the field of biostatistics, and more particularly to methods of classifying high dimensional biological data.

With the wealth of gene expression data from microarrays (such as high density oligonucleotide arrays and cDNA arrays) prediction, classification, and clustering techniques are used for analysis and interpretation of the data. Developments in the field of proteomics are expected to generate vast amounts of protein expression data by quantitating the amounts of a large number of different proteins within a cell or tissue. One can easily imagine carrying out experiments to generate large volumes of data that correlate, e.g., the expression patterns of proteins, mRNAs, cellular complements of membrane lipids, or other metabolic factors to a biologic response (e.g., sensitivity of a cell to a drug), to one of two biologic state (e.g., normal or disease states), or to one of a number of biologic states (e.g., one of a number of different tumor types.) One challenge of dealing with the large numbers of variables sampled using microarray technologies is developing methods to extract meaningful information from the data that can be used to predict or classify the biological state or response of a sample. Such methods would dramatically improve our ability to apply genomics or proteomics data to improve medical diagnoses and treatments.

The use of global gene expression data from microarrays for human cancer research is relatively new (DeRisi et al., 1996). However, since the introduction of DNA microarray technology to quantitate thousands of gene expressions simultaneously (Schena et al., 1995; Lockhart et al., 1996), there have been increasing activities in the area of cancer classification or discrimination. For example, Golub et al. (1999) used a weighted voting scheme for the molecular classification of acute leukemia based on gene expression monitoring from Affymetrix high-density oligonucleotide arrays. Also using Affymetrix oligonucleotide arrays Alon et al. (1999) used a cluster technique based on the deterministic-annealing algorithm to classify cancer and normal colon tissues. Scherf et al. (2000) and Ross et al. (2000) used classical clustering techniques such as average-linkage to cluster tumor tissues from various sites of origin: colon, renal, ovarian, breast, prostate, lung, central nervous system as well as leukemias and melanomas. The popular method of support vector machines ("SVM") introduced by Vapnik was applied to the classification of tumor and normal ovarian tissues by Furey et al. (2000). The use of gene expression profiles to distinguish between negative and positive for BRCA1 mutation (as well as negative and positive for BRCA2 mutation) in hereditary breast cancer was described by Hedenfalk et al. (2001). Some other important applications in human cancer include classifying diffuse large B-cell lymphoma ("DLBCL") (Alizadeh et al., 2000), mammary epithelial cells and breast cancer (Perou et al., 1999, 2000) and skin cancer melanoma (Bittner et al., 2000) based on gene expression data. Dudoit et al. (2000) and Ben-Dor et al. (2000) presented a comparative studies of classification methods applied to various cancer gene expression data. These techniques have also helped to identify previously undetected subtypes of cancer (Golub et al., 1999; Alizadeh et al., 2000; Bittner et al., 2000; Perou et al., 2000). The problem of deriving useful "predictions" from high dimensional data may come in various forms of applications as well, such as, e.g., using expression array data to predict patient survival duration with germinal center B-like DLBCL as compared to compared to those with activated B-like DLBCL using Kaplan-Meier survival curves (Ross et al., 2000).

Gene expression data from DNA microarrays is characterized by many measured variables (genes) on only a few observations (experiments), although both the number of experiments and genes per experiment are growing rapidly. The number of genes on a single array usually is in the thousands, so the number of variables p easily exceeds the number of observations N. Although, the number of measured genes is large there may only be a few underlying gene components that account for much of the data variation; for instance, only a few linear combinations of a subset of genes may account for nearly all of the response variation. Unfortunately, it is exceedingly difficult to determine which genes are members of the subset given the large number of genes, p, and the small number of observations, N. The fact that experiments such as, e.g., microarray experiments that are characterized by many measured variables (e.g., genes), p, on only a relatively few observations or samples, N, renders all statistical methods requiring N>p to be of no direct use.

While this problem has been described with reference to gene expression data from DNA microarrays, similar issues arise with any type of biological data in which the number of variables measured exceeds the number of observations, and the methods of the invention are applicable to many different types of biological data. Thus, there is a need in the art for methods of dealing with such "high dimensional" data (i.e., data that are statistically underdetermined because there are fewer observations, N, than the number of variables, p) to allow classification of biological samples. Methods are needed for binary classification (e.g., to discriminate between two classes such as normal and cancer samples, and between two types of cancers) based on high dimensional data obtained from the sample. Methods also are needed for classification or discrimination of more than two groups or classes ("multi-class"). The need for multi-class discrimination methodologies is apparent in many microarray experiments where various cancer types are simultaneously considered. The present invention addresses these and other shortcomings in the art by providing statistical methods of analyzing biological data to permit accurate classification of samples. The invention uses the method of partial least squares ("PLS") (for binary classification) or the method of multivariate partial least squares ("MPLS") (for multi-class classification) as a dimension reduction technique, followed by a classification step.

BRIEF SUMMARY OF THE INVENTION

It is an object of the invention to provide methods for classifying biological samples from which high dimensional data has been obtained. The methods of the invention permit binary classification (i.e., assignment of a sample to one of two classes), as well as multi-class classification (i.e., assignment of a sample to one of more than two classes). The method involves analyzing data obtained from biological samples with known classifications, carrying out a dimension reduction step on the data, and using the reduced data as input data in a classification step to generate a model useful for predicting the classification of a biological sample with an unknown classification. In one embodiment of the invention, the classification model is binary, i.e., it accounts for only two classes. In this embodiment, the method preferably is carried out using PLS dimension reduction. Classification is then preferably carried out using logistic discrimination ("LD"). In another preferred embodiment of the invention, classification is carried out using quadratic discriminant analysis ("QDA"). In another embodiment, the classification model permits assignment of the unknown sample to one of more than two classes. In this multi-class embodiment of the invention, dimension reduction is preferably carried out using multivariate partial least squares ("MPLS") dimension reduction, and classification is achieved with polychotomous discrimination ("PD") or QDA. In yet another preferred embodiment, a subset of the p variables may be selected according to standard t-statistics, or pairwise comparison and the analysis of variance (ANOVA) prior to the dimension reduction step. The methods of the present invention also permit assessment of the confidence associated with any specific prediction by examining the estimated conditional class probability, $\hat{\pi}$ of a sample.

DETAILED DESCRIPTION OF THE PREFERRED EMBODIMENTS

Figure 1:
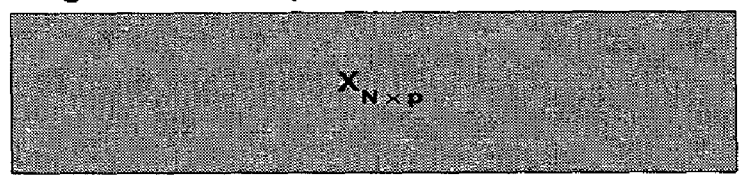
FIG. 1: Illustration of dimension reduction for NC160 data.
Figure 1:
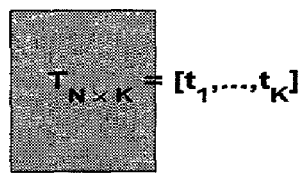
Figure 1:
Figure 1:
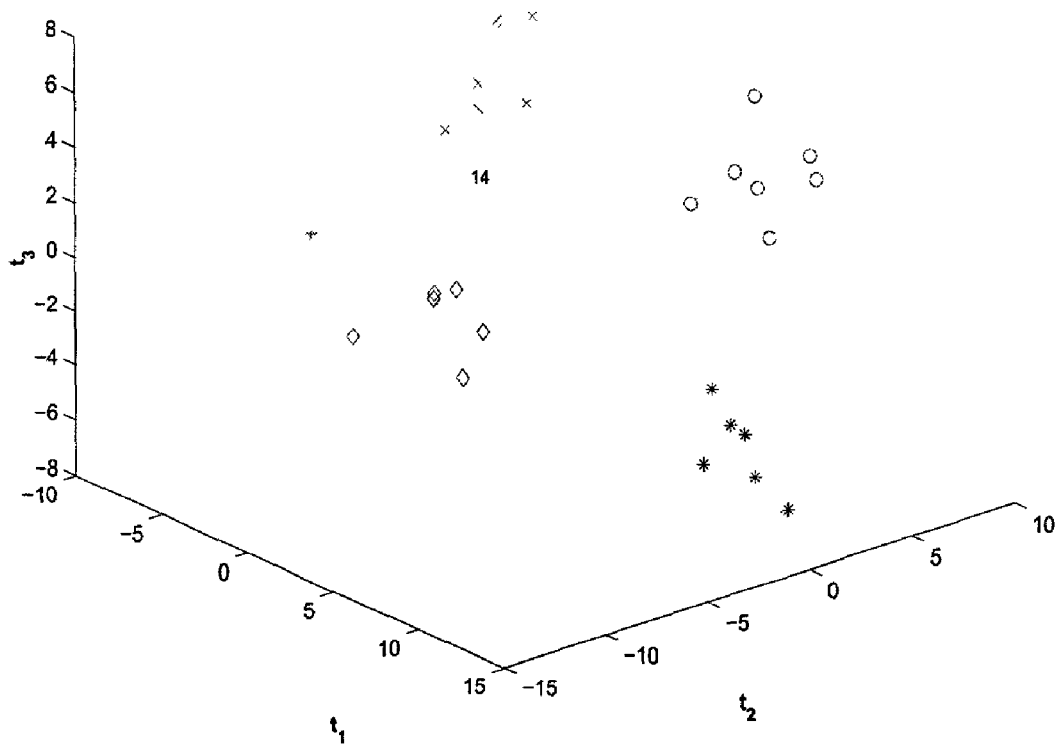

In situations where the number of observations, N, is less than the number of variables, p, (i. e., when N<p), dimension reduction is needed to reduce the high p-dimensional variable space to a lower K-dimensional component space. Under similar data structure in the field of chemometrics, the method of partial least squares ("PLS") has been found to be a useful dimension reduction technique. PLS has been useful as a predictive modeling regression method in the field of chemometrics. For example, in spectroscopy one may be predicting chemical composition of a compound based on observed signals for a particular wavelength, where the number of wavelengths (variables) is large. (Applications of PLS are abundant in the *Journal of Chemometrics* (John Wiley) and *Chemometrics and Intelligent Laboratory Systems* (Elsevier), for example.) An introduction to PLS regression is given by Geladi and Kowalski (1986). The use of PLS in calibration can be found in Martens and Naes (1989). Some theoretical aspects and data-analytical properties of PLS have been studied by chemometricians and statisticians (de Jong, 1993; Frank and Friedman, 1996; Helland, 1988; Helland and Almoy, 1994; Hoskuldsson, 1988; Lorber, Wangen and Kowalski, 1997; Phatak, Reilly, and Penlidis, 1992; Stone and Brooks, 1990; Garwaithe, 1994).

In one aspect, the present invention provides analysis procedures for binary classification ("prediction") of biological samples such as human tumor samples based on high dimensional data such as is obtained from microarray gene expressions measurements. Here, the response variable is a binary vector indicating, e.g., normal or tumor samples, for example. This procedure involves dimension reduction using PLS and classification using methods such as logistic discrimination ("LD"), quadratic discriminant analysis ("QDA"), or linear discriminant analysis. That is, the procedure involves two steps, a dimension reduction step followed by a classification step. According to the methods of the present invention, the PLS components may be modified prior to their use in classification methods. Such modifications include, e.g., singular value decomposition, or linear combinations of univariate logistic regression. The methods may optionally make use of a preliminary screening step to select informative variables prior to dimension reduction by PLS. For binary classifications, t-statistics provides a convenient method for screening. These methods of the invention are illustrated by application to five different microarray data sets involving various human tumor samples: (1) normal versus ovarian tumor samples, (2) acute myeloid leukemia ("AML") versus acute lymphoblastic leukemia ("ALL"), (3) diffuse large B-cell lymphoma ("DLBCL") versus B-cell chronic lymphocytic leukemia ("BCLL"), (4) normal versus colon tumor samples and (5) non-small-cell-lung-carcinoma ("NSCLC") versus renal. To assess the stability of the prediction results and methods we used re-randomization studies (as described in the Methods section, below).

In another aspect, the present invention provides analysis procedures for multi-class classification ("prediction") of biological samples such as human tumor samples based on high dimensional data such as is obtained from microarray gene expression measurements. Here the response variable is a discrete vector indicating, e.g., a particular type of cancer. This aspect of the invention involves multivariate partial least squares ("MPLS") dimension reduction together with a classification step such as polychotomous discrimination ("PD"), quadratic discriminant analysis ("QDA"), or linear discriminant analysis. According to the methods of the present invention, the MPLS components may be modified prior to their use in classification methods. Such modifications include, e.g., singular value decomposition, or linear combinations of univariate logistic regression. Preliminary screening to select information variables prior to dimension reduction by MPLS may be carried out based on pairwise comparison and the analysis of variance (ANOVA) of variables, p. The multi-class classification methods were applied to four cancer gene expression data sets. Specifically; the methodologies proposed in this paper were applied to four gene expression data sets with multiple classes: (a) a hereditary breast cancer data set with (1) BRCA1-mutation, (2) BRCA2-mutation and (3) sporadic breast cancer samples, (b) an acute leukemia data set with (1) acute myeloid leukemia ("AML"), (2) T-cell acute lymphoblastic leukemia ("T-ALL") and (3) B-cell acute lymphoblastic leukemia ("B-ALL") samples, (c) a lymphoma data set with (1) diffuse large B-cell lymphoma ("DLBCL"), (2) B-cell chronic lymphocytic leukemia ("BCLL") and (3) follicular lymphoma ("FL") samples, and (d) the NC160 data set with (1) leukemia, (2) colon, (3) melanoma, (4) renal, and (5) central nervous system ("CNS") samples. The multi-class methods of the invention were further tested using data generated from a simulation gene expression model. The simulation model, procedures, and results are described in the Simulation Studies section. Most technical details are deferred to the Appendix.

Advantages of the present invention over another well-known dimension reduction method, principal components analysis ("PCA") (Massey, 1965; Jolliffe, 1986) were established by comparing results obtained using PLS or MPLS dimension reduction with those from PCA. PCA is used to reduce the high dimensional data to only a few components which explain as much of the observed total variation (such as, e.g., gene expression variation) as possible. This is achieved without regards to the response variation. Components constructed this way are called principal components ("PCs"). In contrast to PCA, PLS components are chosen so that the sample covariance between the response and a linear combination of the p predictors (e.g., genes) is maximum. The latter criterion for PLS is more sensible since there is no a priori reason why constructed components having large predictor variation (e.g., gene expression variation) should be strongly related to the response variable. Certainly a component with small predictor variance could be a better predictor of the response classes. The ability of the dimension reduction method to summarize the covariation between predictors such as gene expressions and response classes should, in principle, yield better prediction results. Thus, for PCA to be competitive, relative to PLS, one can pre-select the predictors which are predictive of the response classes and then apply PCA. Otherwise, one might expect PLS to give better predictions. Using the leukemia data set of Golub et al. (1999) we illustrate a condition that demonstrates the superiority of the PLS dimension reduction approach used by the present invention, relative to PCA in predicting response class.

The organization of this specification is as follows. In the Methods section we describe the dimension reduction methods of PCA, MPLS and PLS, the classification methods of LD, QDA, and PD and predictor selection strategies based on simple t-statistics, and pairwise comparison and the analysis of variance (ANOVA). In the Methods section we also describe the re-randomization technique used to further assess the prediction methods and results. The results from applying the proposed methods to microarray data sets are given in the Results section. Also included in the Results section is the illustration of a condition when PCA fails to predict well relative to PLS. We then conclude and discuss generalizations and other applications of the methods of the invention to microarray gene expression and other high dimensional data.

1. Methods

Traditional statistical methodologies for classification (prediction) do not work when there are more variables, p, than there are samples, N. Specifically, for gene expression data, the number of tissue samples is much smaller than the number of genes. Thus, methods able to cope with the high dimensionality of the data are needed. The present invention relies on a novel combination of dimension reduction with traditional classification methods, such as logistic discrimination, quadratic discriminant analysis, and polychotomous discrimination ("PD") for high dimensional gene expression data. While the invention is illustrated with respect to gene expression data, the methods of the present invention are applicable to any high dimensional biologic data.

1.1. Binary Classification

PLS is the primary dimension reduction method utilized for binary classification, although we also consider the related method of PCA for comparison. The approach taken here consists of two main steps. The first step is the dimension reduction step, which reduces the high dimension p down to a lower dimension K (K<N). Since the reduced dimension, K, is smaller than the number of samples, N, in the second step, one can apply readily available prediction tools, such as logistic discrimination ("LD") or quadratic discriminant analysis ("QDA").

We introduce the method of PLS first by briefly describing the well known and related method of PCA. Classification methods, namely LD and QDA, are also briefly described. Prior to analysis, gene selection may be useful. Hence, we also describe a simple gene selection strategy based on t-statistics.

1.1.1. Dimension Reduction: PCA and PLS

The goal of dimension reduction methods is to reduce the high p-dimensional predictor (gene) space to a lower K-dimensional (component) space. This is achieved by extracting or constructing K components in the predictor space to optimize a defined objective criterion. PCA and PLS are two such methods. To describe these methods some notations are required. Let X be an N×p matrix of N samples and p predictors. Also, let y denote the N×1 vector of response values, such as an indicator of leukemia classes or normal versus tumor tissues.

In PCA the goal is to extract gene components sequentially which maximize the total predictor (e.g., gene expression) variability, irrespective of how well the constructed components predict cancer classes. There is no a priori reason why components with high total predictor variability (e.g., gene expression) should predict cancer classes well. In PCA, orthogonal linear combinations are constructed to maximize the variance of the linear combination of the predictor variables sequentially, $$v_k = \underset{v'v=1}{\mathrm{argmax}} \mathrm{var}^2(Xv) \quad (1)$$

subject to the orthogonality constraint $$v'Sv_j=0, \text{ for all } 1 \leq j < k \quad (2)$$

where S=X'X. The maximum number of nonzero components is the rank of X, which is the same as the rank of X'X. Often in applications of PCA, the predictors are standardized to have mean zero and standard deviation of one. This is referred to as PCA of the correlation matrix, $R_{p \times p}=(1/(N-1))(X-1\bar{x}')'(X-1\bar{x}')$ The constructed principal components (PCs), satisfying the objective criterion (1) are obtained from the spectral decomposition of R, $$R=V\Lambda V', \Lambda=\mathrm{diag}\{\lambda_1 \geq \ldots \geq \lambda_{N-1}\}, \quad (3)$$

where $V=(v_1, \ldots, v_{N-1})$ are the corresponding eigenvectors. The ith PC is a linear combination of the original predictors, $Xv_i$. Roughly, the constructed components summarize as much of the original p predictors' information (variation), irrespective of the response class information.

Note that maximizing the variance of the linear combination of the predictors (e.g., genes), namely var(Xv), may not necessarily yield components predictive of the response variable (such as leukemia classes) because the extracted PCs do not depend on the response vector y, indicating, the class to which the sample belongs For this reason, a different objective criterion for dimension reduction may be more appropriate for prediction.

In contrast to PCA, PLS (orthogonal) components are constructed to maximize the sample covariance between the response values (y) and the linear combination of the predictor (e.g., gene expression) values (X). The objective criterion for constructing components in PLS is to sequentially maximize the covariance between the response variable and a linear combination of the predictors. That is, in PLS, the components are constructed to maximize the objective criterion based on the sample covariance between y and Xw. Thus, we find the weight vector w satisfying the following objective criterion, $$w_k = \underset{w'w=1}{\operatorname{argmax}} cov^2(Xw, y) \qquad (4)$$

subject to the orthogonality constraint $$w'Sw_j=0 \text{ for all } 1 \leq j < \qquad (5)$$

where S=X'X. The maximum number of components, as before, is the rank of X. The ith PLS components are also a linear combinations of the original predictors, $Xw_i$. A basic algorithm to obtain w is given in the Appendix.

Based on the different objective criterion of PCA and PLS, namely var(Xv) and cov(Xw, y), it is reasonable to suspect that if the original p predictors (e.g., genes) are already predictive of response classes then the constructed components from PCA would likely be good predictors of response classes. Therefore, prediction results should be similar to that based on PLS components. Otherwise, one might suspect that PLS should perform better than PCA in prediction. We give examples of this in the Results section.

1.1.2. Classification: LD and QDA

After dimension reduction by PLS and PCA, the high dimension of p is reduced to a lower dimension of K components. Once the K components are constructed we considered prediction of the response classes. Since the reduced dimension is now low (K<N), conventional classification methods such as logistic discrimination and quadratic discriminant analysis can be applied.

Let x be the column vector of p predictor values and y denotes the binary response value. For instance, y=0 for a normal sample, y=1 for a tumor sample and x is the corresponding expression values of p genes. In logistic regression, the conditional class probability, $\pi=P(y=1|x)=P$ (tumor given gene profile x), is modeled using the logistic functional form, $$\pi = \frac{\exp(x'\beta)}{1+\exp(x'\beta)} \qquad (6)$$

The predicted response probabilities are obtained by replacing the parameter β with its maximum likelihood estimate (MLE)$\hat{\beta}$. The predicted class of each sample (as a normal or tumor sample) is $\hat{y}=I(\hat{\pi}>1-\hat{\pi})$, where I(•) is the indicator function; I(A)=1 if condition A is true and zero otherwise. That is, we classify a sample as a tumor ($\hat{y}=1$) if the estimated probability of observing a tumor sample given the gene expression profile, x, is greater than the probability of observing a normal sample with the same gene profile. This classification procedure is called logistic discrimination ("LD"). As mentioned earlier, LD is not defined if N<p. Thus, in order to utilize the LD procedure, we need to replace the original gene profile, x, by the corresponding gene component profile in the reduced space, obtained from PLS or PCA.

Another usual classification method is quadratic discriminant analysis ("QDA") based on the classical multivariate normal model for each class: $x|y=k \sim N_p(\Sigma_k, \mu_k)$, $x \in R^p$ and k=0, 1, ..., G. For binary classification, G=1. The (optimal) classification regions are $$R_k = \{x \in R^p: p_k f_k(x) > p_j f_j(x), j \neq k\} \qquad (7)$$

where $f_k$ is the probability distribution function ("pdf") of x|y=k given above and pk=P(y=k). This is equivalent to classifying a given sample with gene expression profile x into the class with max $\{q_i(x), i=0, 1, ..., G\}$, where $q_i(x)=x'A_i x + c'_i x + c_i$ with $A_i=-0.5\Sigma_i^{-1}$, $c_i=\Sigma_i^{-1}\mu_i$, and $c_i$=log $p_i$ -0.5 log $\Sigma_i$ -0.5$\mu_i'\Sigma_i^{-1}\mu_i$. The posterior probability of membership in class k is $\pi_k=P(y=k|x)=\exp[q_k(x)]/\Sigma_{i=0}^K \exp[q_i x)]$. Again, the full gene profile, x, is replaced by the corresponding gene component profile in the reduced space obtained from PLS or PCA.

Further details on QDA and other classical classification methods can be found in Mardia, Kent, and Bibby (1970), Johnson and Wichern (1992) and Flury (1997). Details on logistic regression can be found in Hosmer and Lemeshow (1989) and McCullagh and Nelder (1989).

1.1.3. Gene Selection

Although the two-step procedure outlined above, namely dimension reduction via PLS followed by classification via LD or QDA, can handle a large number (thousands) of genes, only a subset of genes are of interest in practice. Even after gene selection, often, the number of genes retained is still larger than the number of available samples. Thus, dimension reduction is still needed. It is obvious that good prediction relies on good predictors, hence a method to select the genes for prediction is necessary. For two-class prediction, selection and ranking of the genes can be based on simple t-statistics $$t = \frac{\bar{x}_1 - \bar{x}_2}{\sqrt{s_1^2/N_1 + s_2^2/N_2}} \qquad (8)$$

where $N_k$, $\bar{x}_k$ and $s_k^2$ is the size, mean and variance, respectively, of class k, k=1, 2. For each gene, a t value is computed. We retain a set of the top p* genes, by taking p*/2 genes with the largest positive t values (corresponding to high expression for class 1) and p*/2 genes with smallest negative t values (i.e., those negative t values furthest from zero)(corresponding to high expression for class 2).

We carried out selections to obtain p*=50 genes for the ovarian, leukemia, lymphoma, colon, and NCI60 data. The selection revealed that for the leukemia data set the gene profiles or patterns show a clear differential expression relative to AML/ALL. This is suggestive of the well-known separability of AML/ALL leukemia classes based on gene expression in this data set. However, this differentially expressed pattern was not as clear for normal and ovarian tumor tissue samples or normal and colon tissue samples.

1.1.4. Assessing Prediction Methods and Results

Following gene selection and dimension reduction, we predicted the response classes. The observed error rate can be used to give a rough assessment of a method relative to another. The strength or "confidence" associated with any specific prediction (i.e., for each sample) can be assessed by examining the estimated conditional class probability $\hat{\pi}$ described above.

It is also important to get an idea of how the proposed method will perform in light of new data. However, new data are usually not available, so re-randomization study is an alternative. For re-randomization studies a relatively large sample size, N, is needed. If there are sufficient samples, we carry out a three step procedure to assess the prediction methods. First, we randomly form a training data set consisting of $N_1$ of the N samples. These $N_1$ samples in the training data set are used to fit the model. The remaining $N_2=N-N_1$ samples are saved for model validation (testing). That is, the fitted model is tested on the $N_2$ samples not used to fit the model. This is referred to as out-of-sample prediction.

In the second step, a model is fit to the training data, and the fit to the training data is assessed by leave-out-one cross-validation ("CV"). That is, one of the $N_1$ samples is left out and a model is fitted based on all but the left out sample. The fitted model is then used to predict the left out sample. Leave-out-one CV is used for each of the $N_1$ samples in the training data set. This provides some protection against overfitting, but it is still possible accidentally to select a model that fits the training data especially well due to capitalizing on chance.

The third step assesses the stability of the overall results from steps 1 and 2 by re-randomizations. In the re-randomization step, $N_1$ of the total N samples are randomized into a training data set (with the remaining $N_2$ samples forming the test data set) and then the out-of-sample and leave-out-one CV prediction is repeated on this permuted data set. Averages of prediction rates over repeated re-randomizations can be used to assess the stability of prediction results.

We carried out the re-randomization procedure for the leukemia and lymphoma data sets which contain enough samples. For the ovarian and NCI60 data sets, which contain few samples, we performed only leave-out-one cross-validation ("CV") prediction.

2.1. Multi-Class Classification

Suppose that a qualitative response variable y takes on a finite number of (unordered) values, say 0, 1, ..., G often referred to as classes (or groups). That is, y indicates the cancer type or class 0, 1, ..., or G, for instance. The problem of multi-class cancer classification is to predict the class membership or cancer class based on a vector of gene expression values $x=(x_1, x_2, \ldots, x_p)'$. Most classification methods, such as classical discrimination analysis or polychotomous discrimination are based on the requirement that there are more observations (N) than there are explanatory variables or genes (p). One strategy to approach the problem of classification when N<p is to reduce the dimension of the gene space from p to say K, where K<<N. This is done by constructing K gene components and then classifying the cancers based on the constructed K gene components.

The dimension reduction process is illustrated in FIG. 1 using the NC160 data set consisting of cell lines derived from cancers of various origins. For illustration, we have reduced a gene expression matrix, X of size N×p=35×167, to three gene components, $t_1, t_3, t_3$, using multivariate PLS. It can be seen from the 3-dimensional plot (FIG. 1, bottom) that the three MPLS gene components separate the five cancer classes well (leukemia=*, colon=o, melanoma=+, renal=x, and CNS=◇). Classification methods such as QDA and PD can be used to predict the cancer classes using the K MPLS gene components, here $t_1, t_2$, and $t_3$.

2.1.1. Multivariate Dimension Reduction: Multivariate PLS

When there is more than one response variable, say $y_1, \ldots, y_l$, the objective criterion for maximization (under orthogonality constraints) in multivariate PLS is:

$$\text{cov}^2(Xw, Yc) \qquad (9)$$

where w and c are unit vectors. Since $\text{cov}^2(Xw,Yc)=\text{var}(Xw)\text{corr}^2(Xw, Yc)\text{var}(Yc)$ one can see that using only the correlation term will lead to the well known canonical correlation analysis ("CCA"). The MPLS components are denoted by $t_k$ and are linear combinations of the gene expression values (X) with coefficients given by $w_k$ (satisfying the maximization criterion (9)). The PLS algorithm to obtain w (and c) is simple and fast. (The algorithm can be found in Hoskuldsson (1988), Garthwaite (1994), Helland (1988) or in the context of gene expression data, in the Appendix.)

The response matrix Y in (9) consists of l continuous (or at least ordinal level) response variables, which is the setting MPLS was designed for. However, in the exemplified context, we have a qualitative response variable y consisting of classes 0, 1, ..., G, namely, cancer type 0 through cancer type G. We need to convert or recode the response information indicating cancer class, namely y, into a response matrix Y. To do this with the G+1 cancer classes we created G "design variables" representation (or "reference cell coding") of y. That is, we define the N×G response matrix Y with elements $y_{ik}=I(y_i=k)$ for $i=1, \ldots, N$ and $k=1, \ldots, G$. We have used I(A) to denote the indicator function for event A, so that I(A)=1 if A is true and it is 0 otherwise. (Other strategies for constructing Y are possible.) For example, if G=4 (5 cancer classes), then the vector y consists of values 0, 1, ..., 4 indicating distinct cancer classes 0 through 4. The response matrix Y corresponding to response vector y is displayed for G=4 below $$y = \begin{pmatrix} 0 \\ 1 \\ 2 \\ 3 \\ 4 \end{pmatrix} \rightarrow Y = \begin{pmatrix} 0 & 0 & 0 & 0 \\ 1 & 0 & 0 & 0 \\ 0 & 1 & 0 & 0 \\ 0 & 0 & 1 & 0 \\ 0 & 0 & 0 & 1 \end{pmatrix}$$

Thus, K<<N multivariate PLS gene components, $t_1, \ldots, t_K$, are extracted according to (9) using the original gene expression matrix, X, and the response matrix, Y, constructed from the vector of cancer class indicator y.

2.1.2. Multi-Class Classification Methods

In this section we describe two classification methods that can be applied to make class prediction after dimension reduction. Polychotomous discrimination ("PD") is a generalization of logistic discrimination when there are more than two classes. QDA works for two or more classes so no generalization is needed, but we briefly review the method for completeness of exposition. We also describe in this section a preliminary ranking and selection of the large number of genes used for the analyses.

2.1.3. Polychotomous Discrimination

Assume that the qualitative response variable y can take on finite values, y=k, k∈{0, 1, ..., G}≡o. The distribution of y depends on predictors $x_1, \ldots, x_p$. For example, the kth cancer type (y=k) depends on the p gene expression levels $x_1, \ldots, x_p$ in a given experiment. The response variable y is a G-valued random variable and assume that π(k|x)=P(y=k|x)>0 for all x∈X⊂$R^{p+1}$ and k∈o. For convenience we define the notation $$g_k(x) = \log\left(\frac{\pi(k \mid x)}{\pi(0 \mid x)}\right), \quad \text{for } x \in X \text{ and } k \in O. \quad (10)$$

This is the log of the ratio of the probability of a sample with gene expression profile x being of cancer type k relative to cancer type 0. Often this quantity ($g_k(x)$) is modeled as a linear function of the p gene expressions, x, $$g_k(x) = \log\left(\frac{\pi(k \mid x)}{\pi(0 \mid x)}\right) = \beta_{k0} + \beta_{k1}x_1 + \beta_{k2}x_2 + \cdots + \beta_{kp}x_p = x'\beta_k. \quad (11)$$

Since $\Sigma_{k=0}^G \pi(k|x)=1$, we have $(1-\pi(0|x))/\pi(0|x)=\Sigma_{k=1}^G \exp(g_k(x))$ and it follows that $\pi(0|x)=[1+\Sigma_{k=1}^G \exp(g_k(x))]^{-1}$. For k=1, ..., G, $\pi(k|x)=\exp(g_k(x))[1+\Sigma_{k=1}^G \exp(g_k(x))]^{-1}$ follows from exponentiating (10) and using the identity π(k|x)=[π(k|x)/π(0|x)]π(0|x). Noting that $g_0(x)=0$ for all x∈$R^{p+1}$($\beta_0=0$) we can summarized the conditional class probabilities as $$\pi(k \mid x) = \frac{\exp(g_k(x))}{1 + \sum_{k=0}^{K} \exp(g_k(x))}, \quad x \in X \text{ and } k \in O. \quad (12)$$

This is the probability that a sample with gene expression profile x is of cancer class k. We take (12) as the polychotomous regression model and note that π(k|x)≡π(k|x; β) is a function of v=G(p+1)

parameters $\beta'=(\beta'_1, \ldots, \beta'_K)(\beta \in R^{G(p+1)})$, with $\beta_k=(\beta_{k0}, \beta_{k1}, \ldots, \beta_{kp})'$ (Logistic regression is when K=1 so y is binary (0 or 1)).

An estimate of β is obtained by maximum likelihood estimation ("MLE") and it is described in the Appendix. The MLE of β is denoted $\hat{\beta}$ and it can be obtained (if it exists) when there are more samples than there are parameters, i.e. when N>v=G(p+1). For example, utilizing dimension reduction and predicting 5 cancer classes (G=4) using K=3 gene components requires N>G(K+1)=4(4)=16 samples. Thus, after dimension reduction we can use PD by replacing the full gene profile x by the corresponding gene component profile in the reduced space obtained by MPLS or PCA.

From the estimated coefficient vector $\hat{\beta}$ the estimated conditional class probabilities $\hat{\pi}(k|x)$ k=0, ..., K can be obtained by substituting $\hat{\beta}$ into (12). A given sample with gene expression profile x is then predicted to be of cancer class k with maximum estimated conditional class probability $\hat{\pi}(k|x)$. That is, we classify (or predict) a sample as a cancer of class k if the estimated probability of observing a cancer of this class given the gene expression profile, x, is higher than the probability of observing any other class of cancer given the same gene expression profile.

Further discussions of polychotomous regression can be found, for instance, in Hosmer and Lemeshow (1989, Chap. 8), Kooperberg, Bose, and Stone (1997) and Albert and Anderson (1984).

2.1.4. Quadratic Discriminant Analysis

Another classification method that can be used after dimension reduction is quadratic discriminant analysis ("QDA"). QDA is based on the classical multivariate normal model for each class: x|y=k~$N_p(\Sigma_k, \mu_k)$, x∈$R^p$ and k=0, 1, ... G. (For binary classification, G=1.) The (optimal) classification regions are $$R_k = \{x \in R^p: p_k f_k(x) > p_j f_j(x), j \neq k\} \quad (13)$$

where $f_k$ is the probability density function ("pdf") of x|y=k given above and $p_k$=P(y=k). This is equivalent to classifying a given sample with gene expression profile x into the class with max {$q_i(x)$, i=0, 1, ..., G}, where $q_i(x)=x'A_ix+c'_ix+c_i$ with $A_i=-0.5\Sigma_i^{-1}$, $c_i=\Sigma_i^{-1}\mu_i$ and $c_i=\log p_i-0.5 \log \Sigma_i-0.5\mu'_i\Sigma_i^{-1}\mu_i$. The posterior probability of membership in class k is $\pi_k$=P(y=k|x)=exp[$q_k(x)$]/$\Sigma_{i=0}^K$ exp[$q_i(x)$]. As in PD, the full gene profile, x, is replaced by the corresponding gene component profile in the reduced space obtained from MPLS or PCA.

2.1.5. Multivariate Gene Selection

As in binary classification using univariate PLS described above, the multivariate two-step procedure can handle the number of genes (p) as large as the estimated number of genes in the human genome. However, for any given classification problem it may be advantageous to select the genes which are "good" predictors of the cancer classes. In the binary case, preliminary selection and ranking of the genes based on t-scores works well. For more than two classes, we ranked and selected the genes for multi-class prediction as follows. Recall that the cancer classes are labeled by {0, 1, ..., G}≡o and $x_1, \ldots, x_N$ are the expression values of a gene across the N samples (arrays). We compared all ($_2^{G+1}$) pairwise (absolute) mean differences, $|\bar{x}_k - \bar{x}_{k'}|$ (for k≠k', k, k'∈o) to a critical score $$t\sqrt{MS_E\left(\frac{1}{n_k} + \frac{1}{n_{k'}}\right)} \quad (14)$$

where $MS_E$ (mean squared error) is the estimate of variability from the analysis of variance (ANOVA) model with one factor and G+1 (cancers) groups and t is the $t_{\alpha/2, N-(G+1)}$ value of the t-distribution. Each gene (j=1, ..., p) is ranked according to the number of times the pairwise absolute mean difference exceeded the critical score. Note that this is the least significant difference method in multiple comparison.

For example, the NCI60 data set described in FIG. 1 earlier consists of a subset of the data with five cancer classes: leukemia, colon, melanoma, renal, and CNS labeled respectively as 0, 1, ..., 4=G. Thus, there are ($_2^5$)=10 pairwise absolute mean differences to compare and each gene is ranked as 0, 1, ..., or 10. A zero indicates no pairwise mean difference among the 5 cancer classes and a ten indicates pairwise mean differences among all 10 possible combinations of cancer classes. The p=167 genes chosen for analysis in FIG. 1 are those having ranked as having 7 or more pairwise mean differences according to (14).

3.0 Results

We demonstrate the usefulness of the binary (i.e., univariate) classification methodologies described above to five microarray data sets with various human tumor samples: (1) ovarian (Furey et al., 2000), (2) leukemia (Golub et al., 1999), (3) lymphoma (Alizadeh et al., 2000), (4) colon (Alon et al., 1999) and (5) cancer cell lines from the NCI60 data set (Ross et al., 2000). Data sets (2),(3) and (5) are published data sets and are publicly The ovarian data set is yet to be publish but analyzed results were published by Furey et al. (2000).

The application of the multi-class (i.e., multivariate) classification methodologies is demonstrated by application of the methods to each of four gene expression data sets consisting of human cancer samples: (1) hereditary breast cancer, (2) NCI60 cell lines derived from cancers of various origins, (3) lymphoma, and (4) acute leukemia. These data sets are publicly available.

3.1. Binary Classification

3.1.1. EXAMPLE 1

Ovarian Data

The microarray experiments consist of hybridizations of normal and ovarian tissues on arrays with probes for 97,802 cDNA clones. The ovarian data set considered here consists of 16 normal tissue samples and 14 ovarian tumor tissue samples. The normal tissue samples consist of a spectrum of normal tissues: 2 cyst, 4 peripheral blood lymphocytes, 9 ovary and 1 liver normal tissue. All normal and tumor samples are distinct, coming from different tissues (patients). We log transformed all the gene expression values due to the highly skewed data, typical of gene expression data. The expression of all genes also were standardized to have mean zero and standard deviation of one across samples.

We considered $p^*$=50,100, 500, 1000, 1500 genes selected as described in the Methods section. Since there are few samples, we made leave-out-one CV prediction. Classification of the 30 tissue samples based on K=3 gene components constructed from $p^*$ genes using PLS and PCA are given in Table 1. Overall, the classification results are good. All normal and ovarian tumor samples were correctly classified using LD with PLS and PCs. Results for QDA is the same, except, with PCs one normal (cyst) sample was misclassified ($p^*$=50 and 500). Also, different analyses using $p^*$=1000 and 1500 misclassified one normal ovarian sample. However, all classification methods using PLS gene components are 100% correct for the ovarian data. Furey et al. (2000) also used leave-out-one CV prediction for this data set as well, but using support vector machines ("SVM") (Vapnik, 1998). Although it is not our intent to tune our analyses to theirs to make exact comparisons, a crude observation can be made. Furey et al. reported 3–5 normal samples and 2–4 ovarian tumor samples misclassified using SVM based on 25 to 100 genes. (See Table 1 of Furey et al. Furey et al. included another sample tissue from the same patient. We only use samples from distinct patients since samples should be independent. However, inclusion of this one extra sample did not change the results reported here.)

TABLE 1

Classification results for normal and ovarian tumor samples. Given are the number of correct classification out of 30 samples (16 normal and 14 ovarian tumor samples).

| | LD | | QDA | | Sample |
|---|---|---|---|---|---|
| $p^*$ | PLS | PC | PLS | PC | Misclassified |
| 50 | 30 | 30 | 30 | 29 | #1 |
| 100 | 30 | 30 | 30 | 30 | |
| 500 | 30 | 30 | 30 | 29 | #1 |
| 1000 | 30 | 30 | 30 | 29 | #4 |
| 1500 | 30 | 30 | 30 | 29 | #4 |

The strength or "confidence" in the predictions made can be assessed by examining the estimated conditional class probability, namely $\hat{\pi}=\hat{P}(Y=k|x_i^*)$, k=0, 1, where $x_i^*$ is the gene profile (pattern) in the reduced K-dimensional space. For $p^*$=50 and 100 genes, the estimated conditional probability is essentially one for PLS and the lowest $\hat{\pi}$ is 0.973 for PCA. This holds for $p^*$=1000 and 1500 genes as well. However, for $p^*$=500 genes, two samples were correctly classified (PCA) with moderate estimated conditional class probability of 0.922 and 0.925. Sample 16 is a normal sample from a white blood cell line (HWBC3) and exhibits characteristics of both normal and tumor cells, which makes it a likely candidate for misclassification. SVM had problems classifying this sample (Furey et al., p. 910), but PLS correctly classified this sample as normal tissue.

3.1.2. EXAMPLE 2

Leukemia Data

The data set used here is the acute leukemia data set published by Golub et al. (1999). The original training data set consisted of 38 bone marrow samples with 27 acute lymphoblastic leukemia (ALL) and 11 acute myeloid leukemia (AML) (from adult patients). The independent (test) data set consisted of 24 bone marrow samples as well as 10 peripheral blood specimens from adults and children (20 ALL and 14 AML). Four AML samples from the independent data set were from adult patients. The gene expression intensities were obtained from Affymetrix high-density oligonucleotide microarrays containing probes for 6,817 genes. We log transformed the gene expressions to have a mean of zero and standard deviation of one across samples. No further data preprocessing was applied.

We first applied the methods of the invention to the original data structure of 38 training samples and 34 test samples for $p^*$=50, 100, 500, 1000, and 1500 genes selected as described earlier. The results are given in Table 2. All methods predicted the ALL/AML class correctly 100% for the 38 training samples using leave-out-one CV. Prediction of the test samples using LD based on the training (PLS and PCA) components resulted in one misclassification: sample #66. This is based on $p^*$=50 genes. This AML sample was also misclassified by Golub et al. (1999) using a weighted voting scheme. Participants of the Critical Assessment of Techniques for Microarray Data Mining (CAMDA'00, December 2000) Conference analyzing the leukemia data set all misclassified sample #66. Whether the sample was incorrectly labeled is not known.

TABLE 2

Classification results for the leukemia data set with 38 training samples (27 ALL, 11 AML) and 34 test samples (20 ALL, 14 AML). Given are the number of correct classification out of 38 and 34 for the training and test samples respectively.

| | Training Data (Leave-out-one CV) | | | | Test Data (Out-of-sample) | | | |
|---|---|---|---|---|---|---|---|---|
| | LD | | QDA | | LD | | QDA | |
| p* | PLS | PC | PLS | PC | PLS | PC | PLS | PC |
| 50 | 38 | 38 | 38 | 38 | 33 | 33 | 28 | 30 |
| 100 | 38 | 38 | 38 | 38 | 32 | 32 | 29 | 30 |
| 500 | 38 | 38 | 38 | 38 | 31 | 31 | 32 | 28 |
| 1000 | 38 | 38 | 38 | 38 | 31 | 31 | 31 | 28 |
| 1500 | 38 | 38 | 38 | 38 | 31 | 30 | 30 | 28 |

To assess the stability of the results shown in Table 2 we carried out a re-randomization study as described in the Methods section. We considered an equal random slitting of the N=72 samples: $N_1$=36 training and $N_2$=36 test samples. The analysis above was repeated for 100 re-randomizations. Table 3 gives the average classification rates over the 100 re-randomizations. LD and QDA prediction based on PLS gene components resulted in near perfect classification (between 99% and 100% correct) for the training samples using leave-out-one CV. PCs fared slightly worse (between 90% and 97% correct). This is based on all p* considered. For the test samples, PLS gene components in LD performed better than PCs. However, both PLS and PCs performed similarly in QDA.

TABLE 3

Classification results for re-randomization study of the leukemia data set with 36/36 splitting. Each value in the table is the correct classification percentage averaged over 100 re-randomizations. Perfect classification is 36.

| | Training Data (Leave-out-one CV) | | | | Test Data (Out-of-sample) | | | |
|---|---|---|---|---|---|---|---|---|
| | LD | | QDA | | LD | | QDA | |
| p* | PLS | PC | PLS | PC | PLS | PC | PLS | PC |
| 50 | 36.00 | 34.08 | 35.99 | 34.92 | 34.72 | 33.66 | 34.63 | 34.63 |
| 100 | 35.88 | 33.29 | 35.89 | 34.89 | 34.30 | 32.92 | 34.80 | 34.58 |
| 500 | 36.00 | 34.32 | 36.00 | 35.09 | 34.73 | 34.08 | 34.53 | 34.60 |
| 1000 | 36.00 | 32.95 | 36.00 | 34.57 | 34.82 | 32.50 | 34.77 | 34.09 |
| 1500 | 36.00 | 32.51 | 36.00 | 33.79 | 34.71 | 32.11 | 34.67 | 33.66 |

We also classified the samples based on the 50 "predictive" genes set reported by Golub et al. Leave-out-one CV predictions of the 38 training samples using QDA and LD with PLS gene components resulted in 100% correct and 36/38 for PCs. Based on only the training components, out-of-sample predictions of the 34 test samples were also made. LD with PLS gene components resulted in one misclassification (#66). Golub et al. associated with each prediction a "prediction strength" ("PS"). (For details, see Golub et al.) Five test samples were predicted with low (PS<0.30) to borderline prediction strength: samples #54, 57, 60, 67, and 71 (PS=0.23, 0.22, 0.06, 0.15, and 0.30) with one sample misclassified. These five samples were all correctly classified using LD with PLS gene components with moderate to high conditional class probabilities of 0.97, 1.00, 0.98, 0.89 and 1.00 respectively. Results for all 72 samples are given in Table 4 and re-randomization results, given in Table 5, showed the stability of the estimates.

TABLE 4

50 Genes from Golub et al. Predicted (1 = ALL, 0 = AML) probabilities using leave-out-one CV for original 38 training samples and out-of-sample prediction for the 34 test samples using PLS and PC. PS is the prediction strength from Golub et al. For LD, $\hat{\pi}$ is an estimate of $\pi$ = P(Y = 1|data), and for QDA it is the posterior probability or conditional class probability. Samples marked with an * were misclassified.

| | | | Training Data | | | | | | | Test Data | | | |
|---|---|---|---|---|---|---|---|---|---|---|---|---|---|
| | | | LD | | QDA | | | | | LD | | QDA | |
| i | $y_i$ | PS | $\hat{\pi}_{pls}$ | $\hat{\pi}_{pc}$ | $\hat{\pi}_{pls}$ | $\hat{\pi}_{pc}$ | i | $Y_i$ | PS | $\hat{\pi}_{pls}$ | $\hat{\pi}_{pc}$ | $\hat{\pi}_{pls}$ | $\hat{\pi}_{pc}$ |
| 1 | 1 | 1.00 | 1.00 | 1.00 | 1.00 | 1.00 | 39 | 1 | 0.78 | 1.00 | 1.00 | 1.00 | 1.00 |
| 2 | 1 | 0.41 | 1.00 | 1.00 | 1.00 | 1.00 | 40 | 1 | 0.68 | 1.00 | 1.00 | 1.00 | 1.00 |
| 3 | 1 | 0.87 | 1.00 | 1.00 | 1.00 | 1.00 | 41 | 1 | 0.99 | 1.00 | 1.00 | 1.00 | 1.00 |
| 4 | 1 | 0.91 | 1.00 | 1.00 | 1.00 | 1.00 | 42 | 1 | 0.42 | 1.00 | 1.00 | 1.00 | 1.00 |
| 5 | 1 | 0.89 | 1.00 | 1.00 | 1.00 | 1.00 | 43 | 1 | 0.66 | 1.00 | 1.00 | 1.00 | 1.00 |
| 6 | 1 | 0.76 | 1.00 | 1.00 | 1.00 | 1.00 | 44 | 1 | 0.97 | 1.00 | 1.00 | 1.00 | 1.00 |
| 7 | 1 | 0.78 | 1.00 | 1.00 | 1.00 | 1.00 | 45 | 1 | 0.88 | 1.00 | 1.00 | 1.00 | 1.00 |
| 8 | 1 | 0.77 | 1.00 | 1.00 | 1.00 | 1.00 | 46 | 1 | 0.84 | 1.00 | 1.00 | 1.00 | 1.00 |
| 9 | 1 | 0.89 | 1.00 | 1.00 | 1.00 | 1.00 | 47 | 1 | 0.81 | 1.00 | 1.00 | 1.00 | 1.00 |
| 10 | 1 | 0.56 | 1.00 | 1.00 | 1.00 | 1.00 | 48 | 1 | 0.94 | 1.00 | 1.00 | 1.00 | 1.00 |
| 11 | 1 | 0.74 | 1.00 | 1.00 | 1.00 | 1.00 | 49 | 1 | 0.84 | 1.00 | 1.00 | 1.00 | 1.00 |
| 12 | 1 | 0.20*+ | 1.00 | 0.02* | 1.00 | 0.00* | 50 | 0 | 0.97 | 0.00 | 0.00 | 0.00 | 0.00 |
| 13 | 1 | 1.00 | 1.00 | 1.00 | 1.00 | 1.00 | 51 | 0 | 1.00 | 0.00 | 0.00 | 0.00 | 0.00 |
| 14 | 1 | 0.73 | 1.00 | 1.00 | 1.00 | 1.00 | 52 | 0 | 0.61 | 0.00 | 0.01 | 0.00 | 0.00 |
| 15 | 1 | 0.98 | 1.00 | 1.00 | 1.00 | 1.00 | 53 | 0 | 0.89 | 0.00 | 0.00 | 0.00 | 0.00 |
| 16 | 1 | 0.95 | 1.00 | 1.00 | 1.00 | 1.00 | 54 | 0 | 0.23+ | 0.03 | 1.00* | 0.00 | 0.15 |
| 17 | 1 | 0.49 | 1.00 | 1.00 | 1.00 | 1.00 | 55 | 1 | 0.73 | 1.00 | 1.00 | 1.00 | 1.00 |
| 18 | 1 | 0.59 | 1.00 | 1.00 | 1.00 | 1.00 | 56 | 1 | 0.84 | 1.00 | 1.00 | 1.00 | 1.00 |
| 19 | 1 | 0.80 | 1.00 | 1.00 | 1.00 | 1.00 | 57 | 0 | 0.22+ | 0.00 | 1.00* | 0.00 | 0.03 |
| 20 | 1 | 0.90 | 1.00 | 1.00 | 1.00 | 1.00 | 58 | 0 | 0.74 | 0.08 | 0.00 | 1.00* | 0.01 |
| 21 | 1 | 0.76 | 1.00 | 1.00 | 1.00 | 1.00 | 59 | 1 | 0.68 | 1.00 | 1.00 | 1.00 | 1.00 |

TABLE 4-continued

50 Genes from Golub et al. Predicted (1 = ALL, 0 = AML) probabilities using leave-out-one CV for original 38 training samples and out-of-sample prediction for the 34 test samples using PLS and PC. PS is the prediction strength from Golub et al. For LD, $\hat{\pi}$ is an estimate of $\pi = P(Y = 1|data)$, and for QDA it is the posterior probability or conditional class probability. Samples marked with an * were misclassified.

| | | | Training Data | | | | | | | Test Data | | | |
|---|---|---|---|---|---|---|---|---|---|---|---|---|---|
| | | | LD | | QDA | | | | | LD | | QDA | |
| i | $y_i$ | PS | $\hat{\pi}_{pls}$ | $\hat{\pi}_{pc}$ | $\hat{\pi}_{pls}$ | $\hat{\pi}_{pc}$ | i | $Y_i$ | PS | $\hat{\pi}_{pls}$ | $\hat{\pi}_{pc}$ | $\hat{\pi}_{pls}$ | $\hat{\pi}_{pc}$ |
| 22 | 1 | 0.37 | 1.00 | 1.00 | 1.00 | 1.00 | 60 | 0 | 0.06+ | 0.02 | 1.00* | 0.00 | 0.68* |
| 23 | 1 | 0.77 | 1.00 | 1.00 | 1.00 | 1.00 | 61 | 0 | 0.40 | 0.35 | 1.00* | 1.00* | 0.02 |
| 24 | 1 | 0.82 | 1.00 | 1.00 | 1.00 | 1.00 | 62 | 0 | 0.58 | 0.00 | 0.63* | 0.00 | 0.00 |
| 25 | 1 | 0.43 | 1.00 | 1.00 | 1.00 | 1.00 | 63 | 0 | 0.69 | 0.00 | 0.98* | 0.00 | 0.00 |
| 26 | 1 | 0.89 | 1.00 | 1.00 | 1.00 | 1.00 | 64 | 0 | 0.52 | 0.00 | 0.27 | 0.00 | 0.01 |
| 27 | 1 | 0.82 | 1.00 | 1.00 | 1.00 | 1.00 | 65 | 0 | 0.60 | 0.00 | 0.21 | 0.00 | 0.00 |
| 28 | 0 | 0.44 | 0.00 | 0.00 | 0.00 | 0.00 | 66 | 0 | 0.27*+ | 0.93* | 1.00* | 1.00* | 0.99* |
| 29 | 0 | 0.74 | 0.00 | 0.22 | 0.00 | 0.00 | 67 | 1 | 0.15*+ | 0.89 | 1.00 | 1.00 | 0.20* |
| 30 | 0 | 0.80 | 0.00 | 0.00 | 0.00 | 0.00 | 68 | 1 | 0.80 | 1.00 | 1.00 | 1.00 | 1.00 |
| 31 | 0 | 0.61 | 0.00 | 0.00 | 0.00 | 0.00 | 69 | 1 | 0.85 | 1.00 | 1.00 | 1.00 | 1.00 |
| 32 | 0 | 0.47 | 0.00 | 0.00 | 0.00 | 0.00 | 70 | 1 | 0.73 | 1.00 | 1.00 | 1.00 | 1.00 |
| 33 | 0 | 0.89 | 0.00 | 0.00 | 0.00 | 0.00 | 71 | 1 | 0.30+ | 1.00 | 1.00 | 1.00 | 1.00 |
| 34 | 0 | 0.64 | 0.00 | 0.00 | 0.00 | 0.00 | 72 | 1 | 0.77 | 1.00 | 1.00 | 1.00 | 1.00 |
| 35 | 0 | 0.21+ | 0.00 | 1.00* | 0.00 | 1.00* | | | | | | | |
| 36 | 0 | 0.94 | 0.00 | 0.00 | 0.00 | 0.00 | | | | | | | |
| 37 | 0 | 0.95 | 0.00 | 0.00 | 0.00 | 0.00 | | | | | | | |
| 38 | 0 | 0.73 | 0.00 | 0.00 | 0.00 | 0.00 | | | | | | | |
| #correct | | | 38 | 36 | 38 | 36 | | | | 33 | 27 | 31 | 31 |

TABLE 5

Results from re-randomizations using the 50 genes obtained by Golub et al. Given are average classification rate from all re-randomizations (36 training/36 test samples splitting).

| | LD | | QDA | |
|---|---|---|---|---|
| | PLS | PC | PLS | PC |
| Training Data | 99.56 | 96.44 | 99.56 | 97.00 |
| Test Data | 95.94 | 94.17 | 96.44 | 95.44 |

3.1.3. EXAMPLE 3

Lymphoma Data

The lymphoma data set was published by Alizadeh et al. (2000) and consists of gene expressions from cDNA experiments involving three prevalent adult lymphoid malignancies: diffuse large B-cell lymphoma ("DLBCL"), B-cell chronic lymphocytic leukemia ("BCLL") and follicular lymphoma ("FL"). Each cDNA target was prepared from an experimental mRNA sample and was labeled with Cy5 (red fluorescent dye). A reference cDNA sample was prepared from a combination of nine different lymphoma cell lines and was labeled with Cy3 (green fluorescent dye). Each Cy5 labeled target was combined with the Cy3 labeled reference target and hybridized onto the microarray. Separate measurements were taken from the red and green channels. We analyzed the standardized log relative intensity ratios, namely the log(Cy5/Cy3) values. To test the binary classification procedures of the present invention, we analyzed a subset of the data consisting of 45 DLBCL and 29 BCLL samples with p=4,227 genes.

Using leave-out-one CV, each sample was predicted to be DLBCL or BCLL based on 3 gene components constructed from p*=50, 100, 500 and 1000 genes. The results are given in Table 6. Of the 74 total samples, PLS gene components resulted in either one or two misclassifications at most. The two misclassified samples, #33 and 51, were consistently misclassified. PCs did not performed as well using LD, with at most four misclassifications. However, PCs used with QDA performed similar to PLS components.

TABLE 6

Classification results for DLBCL and BCLL lymphoma samples. Given are the number of correct classification out of 74 samples (45 DLBCL and 29 BCLL samples). Samples misclassified are given in parenthesis on the right side of the table.

| | LD | | QDA | | Sample(s) Misclassified | | | |
|---|---|---|---|---|---|---|---|---|
| p* | PLS | PC | PLS | PC | PLS | PC | PLS | PC |
| 50 | 72 | 73 | 73 | 72 | (33, 51) | (51) | (51) | (33, 51) |
| 100 | 72 | 71 | 72 | 73 | (33, 51) | (9, 33, 51) | (33, 51) | (51) |
| 500 | 72 | 71 | 73 | 73 | (33, 51) | (9, 45, 51) | (51) | (45) |
| 1000 | 72 | 70 | 73 | 73 | (33, 51) | (9, 32, 48, 51) | (51) | (51) |

As with the analysis of the leukemia data, we turned next to re-randomization studies to assess the stability of the classification results. Table 7 summarizes the results of 100 re-randomizations (with 37/37 random split). For this data set, PLS components in LD appear to perform best for leave-out-one CV (of the training data sets). Out-of-sample prediction results for PLS and PCs are similar. On average, classification of the training samples using leave-out-one CV is nearly 100% correct and about less than two misclassifications out of 37 for test samples.

TABLE 7

Classification results for re-randomization study of the lymphoma data set with 37/37 splitting. Each value in the table is the correct classification percentage averaged over 100 re-randomizations. Perfect classification is 37.

| | Training Data (Leave-out-one-CV) | | | | Test Data (Out-of-sample) | | | |
|---|---|---|---|---|---|---|---|---|
| | LD | | QDA | | LD | | QDA | |
| p* | PLS | PC | PLS | PC | PLS | PC | PLS | PC |
| 50 | 36.87 | 36.26 | 36.64 | 35.60 | 35.57 | 36.03 | 35.88 | 35.81 |
| 100 | 36.86 | 36.38 | 36.74 | 36.30 | 35.84 | 36.29 | 36.03 | 36.10 |
| 500 | 36.89 | 35.15 | 36.77 | 35.99 | 35.76 | 35.21 | 35.69 | 35.85 |
| 1000 | 36.83 | 34.94 | 36.90 | 35.68 | 35.58 | 33.87 | 35.32 | 35.12 |

3.1.4. EXAMPLE 4

Colon Data

Alon et al. (1999) used Affymetrix oligonucleotide arrays to monitor expressions of over 6500 human genes with samples of 40 tumor and 22 normal colon tissues. Using a clustering algorithm based on the deterministic-annealing algorithm, Alon et al. clustered the 62 samples into two clusters. One cluster consisted of 35 tumor and 3 normal samples (n8, n12, n34 [the labeling for the 22 normal tissues in Alon et al. are not in consecutive order]). The second cluster contained 19 normal and 5 tumor tissues (T2, T30, T33, T36, T37). (See FIG. 4 of Alon et al.) Furey et al. (2000) did leave-out-one CV prediction of the 62 samples using SVM and six tissues were misclassified, namely (T30, T33, T36) and (n8, n34, n36). As Furey et al. pointed out, the three misclassified tumors (T30, T33, T36) were among the five tumor samples which clustered into the normal group by Alon et al. Also, two normal samples (n8, n34) misclassified by Furey et al. were among the three normal samples clustered into the tumor group by Alon et al.

Classification of tumor and normal colon tissues using the methods of the invention is displayed in Table 8. We carried out analyses for p*=50, 100, 500 and 1000. PLS gene components in LD for 50 and 100 genes performed best with four misclassifications. For p*=50 genes T2, T11, T33, and n36 were misclassified. For p*=100 genes T11, T30, T33, and n11 were misclassified. Note that with the exception of T11 and n11 the samples misclassified here also were misclassified using SVM and by clustering. Note from Table 8 that the PCs analysis is not competitive relative to PLS components for this data set. We also note that gene expression patterns for this data set is quite heterogeneous. Further, the samples that are most commonly misclassified by various methods of analysis have expression patterns that are quite different from their respective groups.

TABLE 8

Classification results for normal and colon tissue samples. Given are the number of correct classification out of 62 samples (40 tumors and 22 normal samples).

| | LD | | QDA | |
|---|---|---|---|---|
| p* | PLS | PC | PLS | PC |
| 50 | 58 | 54 | 57 | 54 |
| 100 | 58 | 53 | 56 | 52 |
| 500 | 56 | 53 | 57 | 53 |
| 1000 | 57 | 52 | 56 | 54 |

3.1.5. EXAMPLE 5

NCI60 Data

The NC160 Data set, published by Ross et al. (2000), consists of samples from human tumor cell lines. The data is from 60 cDNA arrays each containing 9,703 spotted cDNA sequences. The cDNAs arrays contain approximately 8,000 unique genes in 60 human cell lines obtained from various tumor sites: 7 breast, 5 central nervous system ("CNS"), 7 colon, 6 leukemia, 8 melanoma, 9 non-small-cell-lung-carcinoma ("NSCLC"), 6 ovarian, 2 prostate, 9 renal, and 1 unknown. The reference sample used in all hybridizations was prepared by combining an equal mixture of mRNA from 12 of the cell lines. As with the lymphoma (cDNA data) we analyzed the standardized log relative intensity ratios, namely the log(Cy5/Cy3) values. To illustrate our binary classification procedures to this cell lines gene expression data, we selected two of the largest groups: 9 NSCLC and 9 renal samples. Using a subset of 6,814 genes we applied dimension reduction methods to the selected p*=50, 100, 500 and 1000 genes. The results are given in Table 9. PLS gene components predicted all NSCLC and renal cell lines samples correctly 100% in all instances. For each analysis, PCs misclassified only one sample, either sample 4 or 15. The expression patterns of these two misclassified samples are quite different from their respective groups.

TABLE 9

Classification results for NSCLC and renal cell lines. Given are the number of correct classification out of 18 samples (9 NSCLC and 9 renal samples).

| | LD | | QDA | | Sample |
|---|---|---|---|---|---|
| p* | PLS | PC | PLS | PC | Misclassified |
| 50 | 18 | 17 | 18 | 18 | #4 |
| 100 | 18 | 17 | 18 | 18 | #4 |
| 500 | 18 | 18 | 18 | 17 | #15 |
| 1000 | 18 | 18 | 18 | 17 | #15 |

3.1.6. EXAMPLE 6

A Condition When PCs Fail to Predict Well

The conditions under which PLS predicts well have not yet been fully characterized in the statistics or chemometrics literature. In this example we illustrate a condition when PCs fail to predict well, but PLS components continue to predict well. The example given is based on the leukemia data set of Golub et al. (1999).

In the analyses given above, although the results for PLS components were better than that for PCs, the results for PCs were competitive nonetheless. Examining the objective criterion of PLS and PCA, we noted earlier that it would be reasonable to expect predictions based on PCs to be similar to that from PLS if the predictors (e.g., genes) are highly predictive of response (e.g., leukemia classes). This is the case of the analyses based on the 50 predictive genes reported by Golub et al., for instance. However, to see when PCs fail to predict well, while PLS components succeeded, we considered their prediction ability based only on expressed genes, but not exclusively expressed differentially for leukemia classes. This test condition is based on the simple fact that an expressed gene does not necessarily qualify as a good predictor of leukemia classes. For instance, consider a gene highly expressed across all samples, ALL and AML. In this case, the gene will not discriminate between ALL and AML well. We define five nested data sets consisting of all genes expressed on (A) at least one array (p=1,554), (B) 25% (p 1,076), (C) 50% Up 864), (D) 75% (p=662) and (E) 100% (p=246) of the arrays. Note that these genes are expressed but not necessarily differentially expressed for ALL/AML. As before, we applied PLS and PCA to extract three gene components from these five data sets based on the 38 training samples. Predictions of the 38 training samples were based on leave-out-one CV and predictions of the 34 test samples were based on the training components only.

The results are given in Table 10. As can be seen, the decrease in performance of PCs relative to PLS is drastic compared to the result of the 50 predictive genes (Tables 4 and 5). To check the stability of the results in Table 10, we ran 50 re-randomizations. The results are given in Table 11. PCs did much worse relative to PLS gene components in the re-randomizations as well.

TABLE 10

Logistic discrimination and quadratic discriminant analysis of original (38 training/34 test samples splitting) based on class prediction using leave-out-one CV for training data set and out-of-sample prediction for test data set. The five data sets consist of expressed genes, but not all are differentially expressed for AML/ALL.

| Gene Set | % correct, train | | % correct, test | |
|---|---|---|---|---|
| | PLS | PC | PLS | PC |
| | | LD | | |
| Set A | 100.00 | 84.21 | 91.18 | 73.53 |
| Set B | 100.00 | 81.58 | 91.18 | 73.53 |
| Set C | 100.00 | 84.21 | 91.18 | 73.53 |
| Set D | 100.00 | 81.58 | 91.18 | 73.53 |
| Set E | 100.00 | 76.32 | 79.41 | 64.71 |
| | | QDA | | |
| Set A | 100.00 | 84.21 | 91.18 | 82.35 |
| Set B | 100.00 | 84.21 | 94.12 | 82.35 |
| Set C | 100.00 | 81.58 | 91.18 | 82.35 |
| Set D | 100.00 | 81.58 | 91.18 | 88.24 |
| Set E | 100.00 | 57.89 | 71.05 | 50.00 |

TABLE 11

Average classification rates from 50 re-randomizations (36 training/36 test samples splitting) and prediction using leave-out-one CV for training data sets and out-of-sample prediction for test data sets.

| Gene Set | % correct, train | | % correct, test | |
|---|---|---|---|---|
| | PLS | PC | PLS | PC |
| | | LD | | |
| Set A | 99.67 | 86.67 | 93.78 | 82.00 |
| Set B | 99.94 | 87.44 | 94.39 | 83.00 |
| Set C | 99.83 | 89.94 | 93.89 | 83.83 |
| Set D | 99.78 | 85.00 | 94.78 | 83.39 |
| Set E | 97.44 | 73.89 | 89.22 | 69.00 |
| | | QDA | | |
| Set A | 100.00 | 83.44 | 93.17 | 82.39 |
| Set B | 99.94 | 86.33 | 94.28 | 85.00 |
| Set C | 99.72 | 88.28 | 93.50 | 85.17 |
| Set D | 99.78 | 85.00 | 94.78 | 83.39 |
| Set E | 98.06 | 67.28 | 89.61 | 64.89 |

The result here is not surprising since PCA aims to summarize only the variation of the p genes. However, only a subset of p expressed genes is predictive of leukemia classes. Why then do PLS components still perform well in this mixture of expressed genes, both predictive and-non-predictive of leukemia classes? This is most likely attributed to the choice of objective criterion used, namely covariation between the leukemia classes and (the linear combination of) the p genes. Since PLS components are obtained from maximizing cov(Xw, y) it is more able to assign patterns of weights to the genes which are predictive of leukemia classes.

Further indication of this condition, where PCs fail to predict leukemia classes while PLS components succeeded, can be found in the table of response (leukemia classes) and predictor (genes) variation accounted for by the extracted gene components. For example, Table 12(a) summarizes variation explained by the constructed PLS components and PCs for gene set A (p=1, 554). Note that three (K=3) PLS components explained 93.8% of response variation and about 58.7% of predictor variability, compared to three PCs explaining 55.3% and 60.4% respectively. Thus, the total gene variability accounted by PCs and PLS components are similar, but PCs were unable to account for much of the leukemia class variation. Note also that the first PC accounted for 44.5% of total predictor (gene) variability but it accounted for only 2.4% of total response (leukemia class) variability. This is an indicator that it will poorly predict the leukemia classes, as it indeed did (Tables 10 and 11). Now consider the same analysis but with the 50 informative genes. This is given in Table 12(b). This time, the first PC accounted for about 46,3% of predictor variability but also accounted for 84.9% of response (leukemia class) variation-this is a notable increase from 2.4% to 84.9%.

TABLE 12

Variability Explained by PLS components and PCs. The number of components extracted is K.

| | Predictor | | Response | |
|---|---|---|---|---|
| K | Proportion | Cumulative Proportion | Proportion | Cumulative Proportion |
| | (a) Gene set A. | | | |
| | PLS | | | |
| 1 | 26.4713 | 26.4713 | 50.0156 | 50.0156 |
| 2 | 27.1942 | 53.6655 | 26.0319 | 76.0475 |
| 3 | 5.0562 | 58.7217 | 17.7467 | 93.7942 |
| | PC | | | |
| 1 | 44.4644 | 44.4644 | 2.3520 | 2.3520 |
| 2 | 10.5679 | 55.0323 | 38.2658 | 40.6177 |
| 3 | 5.3219 | 60.3542 | 14.6836 | 55.3014 |
| | (b) 50 Predictive genes. | | | |
| | PLS | | | |
| 1 | 46.2635 | 46.2635 | 86.1931 | 86.1931 |
| 2 | 14.7372 | 61.0006 | 3.4223 | 89.6154 |
| 3 | 7.2307 | 68.2314 | 4.4394 | 94.0548 |
| | PC | | | |
| 1 | 46.3143 | 46.3143 | 84.9414 | 84.9414 |
| 2 | 19.3407 | 65.6549 | 0.7407 | 85.6821 |
| 3 | 5.3636 | 71.0185 | 0.1557 | 85.8377 |

4. Binary Classification Conclusions and Discussions

We have introduced statistical analysis methods for the classification of tumors based on microarray gene expression data. The methodologies involve dimension reduction of the high p-dimensional gene expression space followed by logistic classification or quadratic discriminant analysis. We have also illustrated the methods' effectiveness in predicting normal and tumor samples as well as between two different tumor types. The samples varied from human tissue samples to cell lines generated from both one and two channels microarray systems; such as oligonucleotide and cDNA arrays. The methods are able to distinguish between normal and tumor samples as well as between two types of tumors from five different microarray data sets with high accuracy. Furthermore, these results hold under re-randomization studies. Finally, we have also illustrated a condition under which PLS components are superior to PCs in prediction.

The problem of distinguishing normal from tumor samples is an important one. Another problem of interest is in characterizing multiple types of tumors. A data set illustrating this multiple classification problem is the NC160 data set, which contains nine types of tumors. The problem of multiple classification based on gene expression data is much more difficult than the problem of binary classification illustrated the preceding examples. The method of multivariate PLS (Hoskuldsson, 1988; Garthwaite, 1994) is useful for this problem as illustrated in the following section.

The PLS method can be of use for gene expression analysis in other contexts as well. Predicting the expressions of a target gene based on the remaining mass of genes is one example. Here, PLS is used to reduce the dimension of the predictors and then multiple linear regression (or another prediction method for continuous response) is used to predict the expressions of the target gene. Quantifying the predicted gene expression values such that they are compatible with some clinical outcomes is of practical value.

Another related problem which is amenable to analysis using the methods of the invention include assessing the relationship between cellular reaction to drug therapy and their gene expression pattern. For example, Scherf et al. (2000) assessed growth inhibition from tracking changes in total cellular protein (in cell lines) after drug treatment. Here, the response of cell lines to each drug treatment are the response variables, y. Associated with the cell lines are their gene expressions, p. Since the expression patterns are from those of untreated cell lines, Scherf et al. focused on the relationship between gene expression patterns of the cell lines and their sensitivity to drug therapy. This relationship can be studied via a direct application of the univariate or multivariate PLS methods of the invention, which can handle the high dimensionality of the data.

Another example, in cancer research, is the prediction of patient survival times based on gene expressions. For example, Ross et al. (2000) compared patient survival duration with germinal center B-like DLBCL compared to those with activated B-like DLBCL using Kaplan-Meier survival curves (Kaplan and Meier, 1958). These groups were determined by gene expression analysis. A more general and useful approach is to model the observed survival (and censored) times, y, as a function of the p gene expressions. A common tool widely used for this purpose is the proportional hazard regression proposed by Cox (1972). Again, straight-forward application of this method is not possible since N<p. Hence, dimension reduction is needed, however, care is needed to address the observed censored times. Our work indicates that the PLS methods of the invention are of use in this context as well.

4.1. Multi-Class Classification

4.1.1. EXAMPLE 7

Hereditary Breast Cancer Data

Hedenfalk and co-workers (2001) studied gene expression patterns in hereditary breast cancer. In particular, many cases of hereditary breast cancer are attributed to individuals with a mutant BRCA1 or BRCA2 gene. Breast cancers with BRCA1 or BRCA2 mutation have pathologically distinct features (e.g., high mitotic index, noninfiltrating smooth edges and lymphocytic infiltrate, grade level; see Hedenfalk et al., p. 539–540). Furthermore, distinctive features of BRCA1 and BRCA2 cancers are used to distinguish them from sporadic cases of breast cancers. Previous experimental evidence indicates that generally cancers with BRCA1 mutation lacks both estrogen and progesterone receptors but these hormones receptors are present in those with BRCA2 mutations (Karp et al., 1997; Johannsson et al., 1997; Loman et al., 1998; Verhoog et al., 1998). Also, functional BRCA1 and BRCA2 proteins are involved in the repairing of damaged DNA, hence, cells with the mutant genes have decreased ability to participate in DNA repair.

Hedenfalk et al. (2001) monitored the global expression patterns of 7 cancers with BRCA1 mutation, 8 with BRCA2 mutation, and 7 sporadic cases of primary breast cancers using cDNA microarrays. (See Table 1, p. 543 of Hedenfalk et al. for a summary of the characteristics of all 22 samples.) There were 6,512 cDNA used which represent 5,361 unique genes. Among the 5,361 genes 2,905 are known and 2,456 are unknown genes. Selected for analysis were p=3,226 genes and these are available publicly.

The varied phenotypes and pathways to cancer formation induced by BRCA1 and BRCA2 mutation suggest that the gene expression patterns of breast cancer samples between these mutations or lack thereof may be distinct. In the framework of classification or class prediction, one can ask whether the gene expression patterns can be used to predict BRCA1-mutation-positive versus BRCA1-mutation-negative. This would be done by pooling the 8 samples with BRCA2 mutation with the 7 sporadic cases of breast cancer into one group. Similarly, the 7 samples with BRCA1 mutation can be pooled with the 7 sporadic samples into one group to make class prediction for BRCA2-mutation-positive versus negative. However, such "one-versus-all" classification is not completely satisfactory since distinct differences between all three classes (BRCA1-mutation, BRCA2-mutation, and sporadic) is expected at the measured mRNA level. Thus, we considered multi-class cancer classification methods to predict each sample as a breast cancer with BRCA1 mutation, BRCA2 mutation or as sporadic breast cancer based on the observed gene expression profiles of the samples belonging to the three cancer classes.

Preliminary ranking and selection of the genes for analysis was carried out as described earlier in the multivariate gene selection section. The number of genes with 0, 1, 2, or 3 pairwise absolute mean differences exceeding the critical score is 2269, 541, 405, or 11 respectively. Thus, of the 3,226 genes 2,269 showed no pairwise absolute mean difference and only 11 genes showed all 3 pairwise differences. Note that 405 genes showed 2 pairwise differences, however, this does not mean that they can not discriminate amongst the three cancer classes. Taken together, these genes present a global expression pattern that can be used to discriminate among the three cancer classes. The subset of genes selected for analysis is denoted by p*. We considered two analyses based on p*=11 (genes with all 3 pairwise differences) and p*=416 (genes with at least 2 pairwise differences).

We applied multivariate PLS and PCA to reduce the dimension from p*=11 or p*=416 to K=3 MPLS gene components and 3 PCs respectively. All analyses were based on standardized log expression ratios. Prediction of each of the N=22 samples as BRCA1, BRCA2, or as sporadic was carried out using PD and QDA based on the constructed gene components. Prediction results were based on leave-out-one cross-validation (CV).

The results are summarized in Table 13. PD using MPLS gene components correctly classified all 22 samples using either p*=11 or p*=416 genes. For p*=416, MPLS components in QDA and PCs in PD also correctly predicted all samples into their cancer classes. For this data set MPLS gene components performed better than PCs in both PD and QDA.

TABLE 13

Hereditary breast cancer data. N = 22, $n_1$ = 7 (BRCA1), $n_2$ = 8 (BRCA2), and $n_3$ = 7 (sporadic). Given are the number of misclassification out of N = 22 samples and in parenthesis are the samples misclassified with superscript 1, 2 and s indicating BRCA1, BRCA2 and sporadic respectively.

| | PD | | QDA | | #Pairwise Absolute |
|---|---|---|---|---|---|
| p* | MPLS | PCA | MPLS | PCA | Mean Difference |
| 11 | 0 | 1(#16$^s$) | 2(#2$^1$, 15$^2$) | 3(#2$^1$, 13$^2$, 21$^s$) | 3 |
| 416 | 0 | 0 | 0 | 2(#16$^s$, 20$^s$) | ≥2 |

An interesting sporadic sample misclassified by PCs using QDA (p*=416) is sample 20. When classifying all samples as either BRCA1-mutation-positive versus negative (binary classification) Hedenfalk et al. misclassified this sporadic sample as having a BRCA1 mutation. We obtained similar results using the binary classification methods of the invention described above. Studies have suggested that abnormal methylation of the promoter region is indicative of inactivation of the BRCA1 gene (Catteau et al., 1999; Esteller et al., 2000); therefore, such samples show similar phenotypes as samples with BRCA1 mutation. Thus, such samples are potential candidates for misclassification when using data at the molecular level. However, expression patterns (or lack thereof) of an inactivated gene is not identical to that of a mutated gene. It is reasonable that if one looks at a large class of genes simultaneous subtle expression patterns emerges which can be predictive of cancer classes.

4.1.2. EXAMPLE 8

NC160 Data: Cell Lines Derived from Various Cancer Sites

The NCI60 data set was introduced earlier (see FIG. 1) to illustrate the process of dimension reduction. This data set is from Ross et al. (2000) and Scherf et al. (2000). The data is from 60 cDNA arrays each containing 9,703 spotted cDNA sequences. The cDNAs arrays contain approximately 8,000 unique genes in 60 human cell lines obtained from various cancer sites. The reference sample used in all hybridizations was prepared by combining an equal mixture of mRNA from 12 of the cell lines. For illustration of the application of the multi-class classification methods to cancer classification, we considered classification of 6 cancer types: leukemia ($n_1$=6), colon ($n_2$=7), melanoma ($n_3$=8), renal ($n_4$=8), and CNS ($n_5$=6).

We analyzed the standardized log relative intensity ratios, namely the log(Cy5/Cy3) values. Specifically, we used a subset of 1,376 genes and 40 individually assessed targets (p=1,416) analyzed by Scherf et al. (2000) relative to drug activities of the same cell lines, which is publicly available. For this data set there are some missing gene expression values. Genes with 2 or fewer missing values (out of 35) were included for analysis by replacing the (1 or 2) missing values with the median of the gene's expression. This resulted in a subset of 1,299 genes which we used for analysis.

Applying the preliminary gene ranking procedure resulted in the following ranking of the genes: 167 (0), 76 (1), 115 (2), 119 (3), 266 (4), 148 (5), 241 (6), 109 (7), 53 (8), 5 (9), 0 (10). That is, 167 genes showed no pairwise absolute mean difference, 76 genes showed 1 pairwise difference, etc. We pooled all genes showing at least 8 pairwise differences (p*=58) and also all genes showing at least 7 pairwise differences (p*=167) for analysis. As before dimension reduction via MPLS and PCA and classification using PD and QDA were then used to predict the cancer class of each sample.

The classification results based on leave-out-one CV are displayed in Table 14. With p*=58 genes 3 MPLS gene components and PCs correctly classified all cancer classes using PD. Three MPLS gene components constructed from p*=167 genes also correctly classified all cancer classes with PD. These components are plotted in FIG. 1, which illustrates dimension reduction for NCI60 data. In FIG. 1 the NCI60 data, the "original" gene expression data set used here is $X_{35 \times 167}$ and K=3 PLS gene components are constructed giving $T_{35 \times 3}$=[$t_1$, $t_2$, $t_3$]. The 3-dimensional PLS gene components plot, illustrates the separability of the cancer classes: leukemia=*, colon=o, melanoma=+, renal=x, and CNS=◇. As shown in Table 14, QDA did not perform as well as PD, with one misclassification when using MPLS gene components (both p*=58 and 167). This commonly misclassified sample (#14), a melanoma sample, is marked in FIG. 1 (bottom) and it can be seen that the sample does not group with the other melanoma samples.

TABLE 14

NCI60 data: 5 cancer classes. N = 35, $n_1$ = 6 (leukemia), $n_2$ = 7 (colon), $n_3$ = 8 (melanoma), $n_4$ = 8 (renal) and $n_5$ = 6 (CNS). Given are the number of misclassification out of N = 35 samples and in parenthesis are the samples misclassified with superscript le, co, me, re, and cn indicating leukemia, colon, melanoma, renal, and CNS respectively.

| | PD | | QDA | | #Pairwise Abs. |
|---|---|---|---|---|---|
| $p^*$ | MPLS | PCA | MPLS | PCA | Mean Difference |
| 58 | 0 | 0 | 1(#14$^{me}$) | 3(#1$^{le}$, 14$^{me}$, 30$^{cn}$) | $\geq 8$ |
| 167 | 0 | 3(#29$^{re}$, 31$^{cn}$, 34$^{cn}$) | 1(14$^{me}$) | 5(#14$^{me}$, 26$^{re}$, 29$^{re}$, 31$^{cn}$ 34$^{cn}$) | $\geq 7$ |

4.1.3. EXAMPLE 9

Lymphoma Data

The lymphoma data set was published by Alizadeh et al. (2000) and consists of gene expressions from cDNA experiments involving three prevalent adult lymphoid malignancies: diffuse large B-cell lymphoma ("DLBCL"), B-cell chronic lymphocytic leukemia ("BCLL") and follicular lymphoma ("FL"). Each cDNA target was prepared from an experimental mRNA sample and was labeled with Cy5 (red fluorescent dye). A reference cDNA sample was prepared from a combination of nine different lymphoma cell lines and was labeled with Cy3 (green fluorescent dye). Each Cy5 labeled target was combined with the Cy3 labeled reference target and hybridized onto the microarray. Separate measurements were taken from the red and green channels. We analyzed the standardized log relative intensity ratios, namely the log(Cy5/Cy3) values.

The lymphoma data set consists of N=83 samples of three cancer classes: 45 are DLBCL, 29 are BCLL and 9 are FL. Previously we tested binary classification using analogous dimension reduction and classification methods on this data set using only the two largest groups (DLBCL and BCLL) (Nguyen and Rocke, 2001). Now, we consider multi-class cancer classification of all 3 classes simultaneously. We analyze a subset of the data consisting of p=4,151 genes. Preliminary ranking and selection of the p genes were performed as described in the multivariate gene selection section. The procedure resulted in 2,168 genes with 0 pairwise absolute mean difference, 1,003 with 1,896 with 2, and 84 with all 3 pairwise absolute mean expression difference.

Using leave-out-one CV, each sample was predicted to be DLBCL, BCLL, or FL based on 3 gene components constructed from $p^*=84$ genes (with all 3 pairwise mean differences) and $p^*=980$ genes (with at least 2 pairwise mean differences). The results are given in Table 15. For PD MPLS gene components performed better than PCs with two misclassifications (97.6%). However, for this data set QDA performed best with only one misclassification (98.8%). A BCLL sample (#51) was misclassified by all (eight combinations) of the methods. MPLS gene components performed better than PCs for $p^*=84$ and the results are equal for $p^*=980$.

TABLE 15

Lymphoma data: N = 83, $n_1$ = 45 (DLBCL), $n_2$ = 29 (BCLL), $n_3$ = 9 (FL). Given are the number of misclassification out of N = 83 samples and in parenthesis are the samples misclassified with superscript D, B and F indicating DLBCL, BCLL and FL respectively.

| | PD | | QDA | | #Pairwise Abs. |
|---|---|---|---|---|---|
| $p^*$ | MPLS | PCA | MPLS | PCA | Mean Difference |
| 84+ | 2 | 5 | 3 | 6 | $\geq 2$ |
| 980 | 4 | 4 | 1 | 1 | 3 |

| | $p^* = 84$ | | $p^* = 980$ |
|---|---|---|---|
| MPLS-PD | (#9$^D$, 51$^B$) | MPLS-PD | (#9$^D$, 32$^D$, 48$^B$, 51$^B$) |
| PCA-PD | (#9$^D$, 11$^D$, 18$^D$, 55$^D$) | PCA-PD | (#9$^D$, 32$^D$, 48$^B$, 51$^B$) |
| MPLS-QDA | (#5$^D$, 11$^D$, 51$^B$) | MPLS-QDA | (#51$^B$) |
| PCA-QDA | (#9$^D$, 11$^D$, 18$^D$, 51$^B$, 55$^B$, 75$^F$) | PCA-QDA | (#51$^B$) |

+Model without intercept.

4.1.4. EXAMPLE 10

Acute Leukemia Data

The data set used here is the acute leukemia data set published by Golub et al. (1999). The original training data set consisted of 38 bone marrow samples with 27 acute lymphoblastic leukemia ("ALL") and 11 acute myeloid leukemia ("AML") (from adult patients). The independent (test) data set consisted of 24 bone marrow samples as well as 10 peripheral blood specimens from adults and children (20 ALL and 14 AML). It has been noted that global expression patterns of T-cell ALL ("T-ALL") and B-cell ALL ("B-ALL") are distinct and can be used to differentiate between the two sub-classes of ALL (Golub et al., 1999). Thus, for multi-class cancer discrimination we pooled the two data sets to obtain N=72 samples with three cancer classes: (1) AML ($n_1$=25), (2) B-ALL ($n_2$=38) and (3) T-ALL ($n_3$=9).

The gene expression intensities were obtained from Affymetrix high-density oligonucleotide microarrays containing probes for 6,817 genes. We log transformed the gene expressions to have a mean of zero and standard deviation of one across samples. For the subsequent analyses we used a subset of p=3,490 genes. As in the analyses of the previous data sets we first ranked the genes. The procedure resulted in 1,945 genes with 0 pairwise absolute mean difference, 732 with 1,719 with 2, and 84 with all 3 pairwise absolute mean expression differences.

As before, using leave-out-one CV, each sample was predicted to be AML, B-ALL, or T-ALL based on 3 gene components constructed from p*=94 genes (with all 3 pairwise mean differences) and p*=813 genes (with at least 2 pairwise mean differences). The results are given in Table 16. Classification methods compared similarly as for the lymphoma data set. Best classification results come from QDA with MPLS components constructed from p*=813 genes (all correct) and from p*=94 genes (1 incorrect). In all eight analyses combined there were 4 samples which were misclassified: two B-ALL (#12, 17), one AML (#66), and one T-ALL (#67).

TABLE 16

Acute leukemia data: N = 72, $n_1$ = 25 (AML), $n_2$ = 38 (B-ALL), and $n_3$ = 9 (T-ALL). Given are the number of misclassification out of N = 72 samples and in parenthesis are the samples misclassified with superscript A, B and T indicating AML, B-ALL and T-ALL respectively.

|  | PD | | QDA | | # Pairwise Absolute |
| --- | --- | --- | --- | --- | --- |
| p* | MPLS | PCA | MPLS | PCA | Mean Difference |
| 94 | 4 | 4 | 1 | 3 | ≧2 |
| 813 | 3 | 4 | 0 | 2 | 3 |

|  | p* = 94 |  | p* = 813 |
| --- | --- | --- | --- |
| MPLS-PD | (#12[B], 17[B], 66[A], 67[T]) | MPLS-PD | (#17[B], 66[A], 67[T]) |
| PCA-PD | (#12[B], 17[B], 66[A], 67[T]) | PCA-PD | (#12[B], 17[B], 66[A], 67[T]) |
| MPLS-QDA | (#12[B]) | MPLS-QDA | (none) |
| PCA-QDA | (#12[B], 66[A], 67[T]) | PCA-QDA | (#12[B], 67[T]) |

4.1.5. EXAMPLE 11

Simulation Studies

We have tested the proposed methodologies for mult-class cancer classification on four gene expression data sets. To further study the performance of the proposed methodologies we designed a simulation model and procedure for simulating gene expression data. The proposed methodologies are applied the simulated data to assess the relative performance. The simulation model presented here is for multi-class but a similar simulation was carried out for the binary classification (Nguyen and Rocke, 2000). More details can be found there.

4.1.6. Simulation Model and Procedure

It is sensible in dimension reduction techniques (such as PCA) to use the total variability to describe a given data set. Certain physical mechanisms, such as DNA microarray technology, seem to generate data with a few underlying factors or components that explain a large amount of the total variability. The simulated data matrices are generated to mimic this physical process. For instance, if it is assumed that the data have only a few underlying components then the data matrix X generated should reflect this observation. For flexibility in comparing the performances of various statistical methods, however, the data matrix X is generated so that the first few PCs account for a specified proportion of total variability. We then generated data with a spectrum of total variability ranging from 30% to 90%, which encompasses total gene variability of nearly all real gene expression data that we have observed.

We now describe the method of generating the data. The ith row of the N×p data matrix is generated as follows. Generate $$x_i^* = r_{1i}\tau_1 + \ldots + r_{di}\tau_d + \epsilon_i \quad i=1, \ldots, N \quad (15)$$

$$\text{or } x_{ij}^k = \sum_{k=1}^{d} \tau_{ki}\tau_{kj} + \varepsilon_{ij}(j = 1, \ldots, p) \text{ where}$$

$$\tau_k = (\tau_{k1}, \ldots, \tau_{kp})' (k = 1, \ldots, d), \epsilon_i = (\varepsilon_{i1}, \ldots, \varepsilon_{ip})'$$

is a vector of i.i.d. noises, and $\{r_{1i}, \ldots, r_{di}\}$ is a set of constants. We used the models $$\tau_{kj} \text{ i.i.d. } N(\mu_\tau, \sigma_\tau^2)$$

$$\epsilon_{ij} \text{ i.i.d. } N(0, \sigma_\epsilon^2). \quad (16)$$

Elements of the ith row of X is obtained as $$x_{ij} = exp(x_{ij}^*) \, j=1, \ldots, p. \quad (17)$$

This model was proposed in Nguyen and Rocke (2000) and a study of the choices of $\mu_\epsilon$, $\mu_\tau$, and ratio of standard deviation $\sigma_\epsilon/\sigma_\tau$ as well as details of simulation parameters were discussed there.

After the generation of the data matrix X the true probabilities are generated according the to polychotomous regression model, $$\pi_i = (\pi(0|x_i), \pi(1|x_i), \ldots, \pi(K|x_i))$$

where $$\pi(k \mid x_i) = \frac{exp(g_k(x_i))}{1 + \sum_{k=0}^{K} exp(g_k(x_i))}, i = 1, \ldots, N \text{ and } k = 0, 1, \ldots, G. \quad (18)$$

The true coefficient vector are assume fixed, but are actually generated from a $N(0, \sigma_\tau^2)$ distribution and the simulation parameter $\sigma_r^2$, are chosen in conjunction with $\mu_\epsilon$, $\mu_{96}$ and ratio of standard deviation $\sigma_\epsilon/\sigma_\tau$. (The effect of these simulation parameters are discussed and given in Nguyen and Rocke (2000).) The response variable Y is generated according to the vector π of true probabilities. That is, for classes 0, 1, ..., G generate the G×1 multinomial vector, $$z_i \sim \text{Mult}(1, \pi_i), i=1, \ldots, N. \quad (19)$$

Note that $z_i$ is a vector with a single entry of one and the rest are zeros. If $Z_{ik}$ (k=0, 1; ..., G) is one in the kth entry then the observed response is $y_i$=k. Thus, for N random samples $(z_1, \ldots, z_N)$ we obtain the response vector $y = (y_1, \ldots, y_N)'$ with $y_i \epsilon o$.

We generated 100 data sets each of size N×p for N60 and various p=100, 300, 500, 800, 1000, 1200, 1400 and 1600 (total of 800 N×p datasets). Four sets of simulation (total 3,200) datasets are generated so that three PCs explain about 30%, 50%, 70% and 90% of total predictor variability: ave(λ, 3)=($\lambda_1 + \lambda_2 + \lambda_3$/p). (The actual datasets generated achieved the percentages of 27%; 47%, 70% and 90%.) The generated response variable contains four groups (G=3). For each data set, three multivariate PLS components and PCs were extracted and classification was performed using (1) PD (2) QDA with direct resubstitution and (3) QDA with leave-out-one cross-validation (Lachenbruch and Mickey; 1968). The results are summarized in the next section.

4.1.7. Simulation Results

Figure 2:
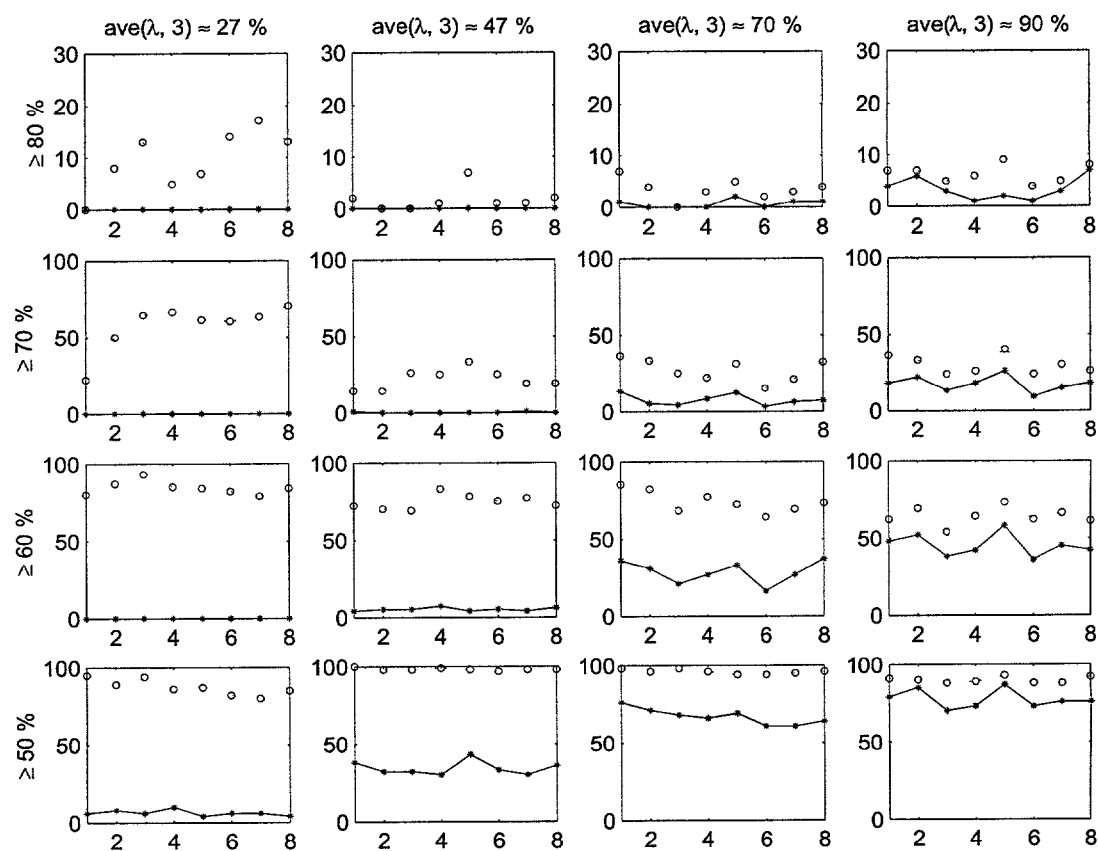
FIG. 2: Polychotomous discrimination using multivariate partial least squares ("MPLS") components and principal components ("PCs").
Figure 3:
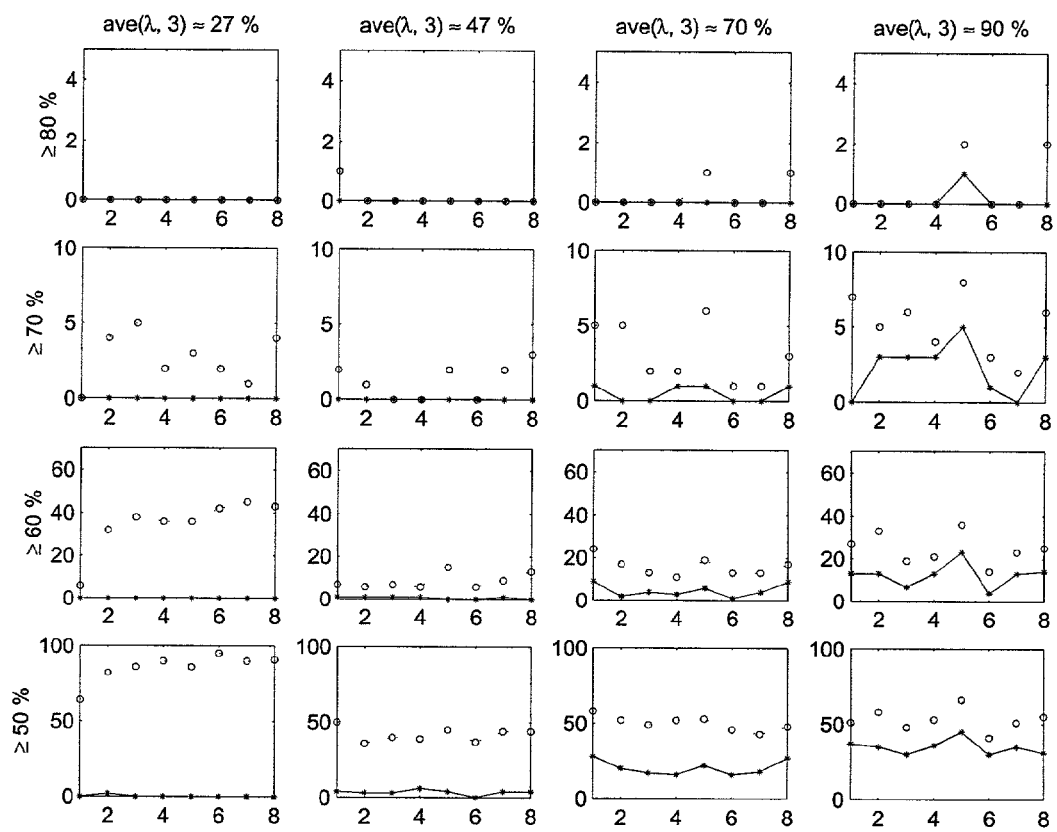
FIG. 3: Quadratic discriminant analysis ("QDA") with leave-out-one cross validation ("CV") using MPLS components and PCs.
Figure 4:
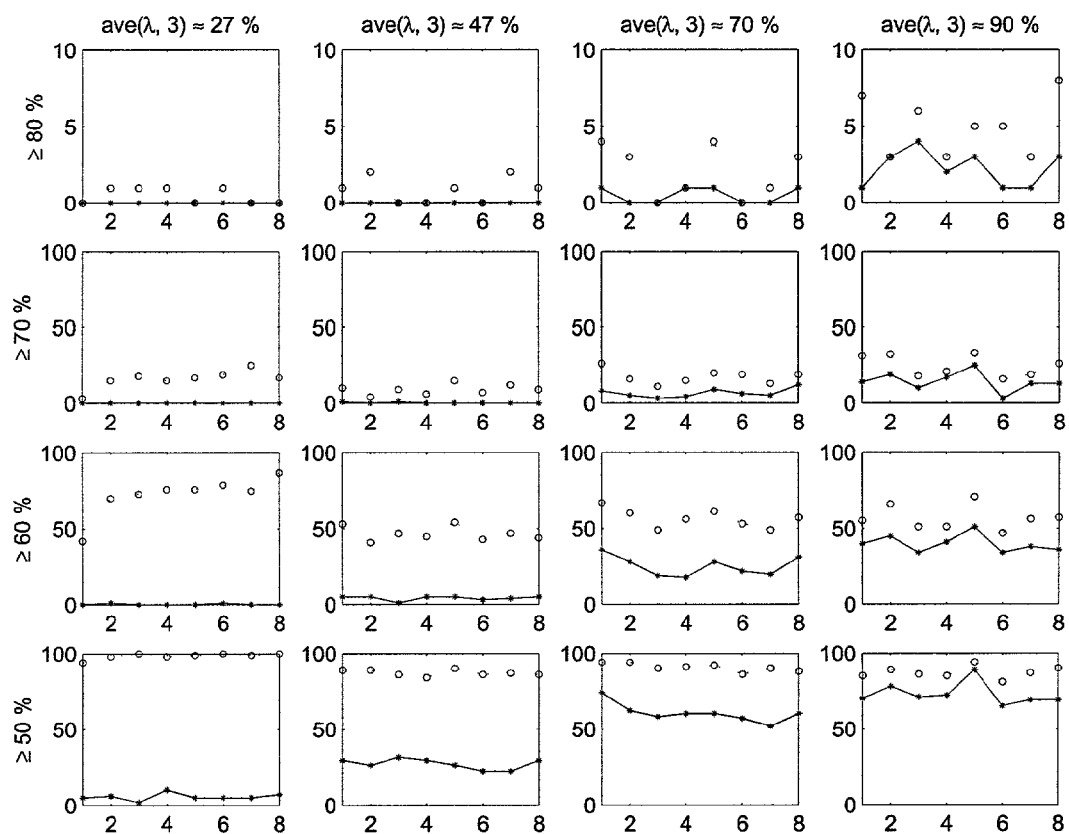
FIG. 4: QDA with direct-resubstitution using MPLS components and PCs.

We first compare classification using multivariate PLS components and PCs using (1) PD, (2) QDA with direct resubstitution, and (3) QDA with leave-out-one cross-validation. Although the nominal percentage level of correct classification is lower in the multiple class setting than the binary case the general results are similar. Classification using multivariate PLS components out performs classification using PCs. As the percentage of total predictor variability accounted for by the extracted PCs increases (ave($\lambda$, 3)=27%, 47%, 70%, 90%) classification based on PCs improves. Despite the improvement MPLS out performs PCs; in fact the performance of MPLS appears not to be influenced by the percentage of total predictor variability accounted for by the extracted PCs. The results are summarized in FIG. 2. FIG. 2 illustrates PD using MPLS (•o•) components & PCs (-*-). Percentage of correct classification using PD with MPLS components and PCs. Each row (of plots) correspond to percentage correct classification ≧80%, ≧70%, ≧60%, ≧50%. Each column is the percentage of total predictor variation accounted for by three PCs, ave ($\lambda$,3). The x-axis is the number of variables p (1→p=100, 2→p=300, 3→p=500, 4→p=800, 5→p=1,000, 6→p=1,200, 7→p=1,400, 8→p=1,600). The y-axis gives the number out of 100 datasets generated with percentage of correct classification ≧80%, ≧70%, ≧60%, ≧50%. Thus, MPLS components appear to perform better than PCs using PD under the simulation model. This is also true with the QDA method using direct resubstitution (FIG. 4) as well as QDA using leave-out-one cross-validation (FIG. 3). FIG. 3 illustrates QDA with leave-out-one CV using MPLS components and PCs. Each row (of plots) correspond to percentage correct classification ≧80%, ≧70%, ≧60%, ≧50%. Each column is the percentage of total predictor variation accounted for by three PCs, ave ($\lambda$,3). The x-axis is the number of variables p (1→p=100, 2→p=300, 3→p=500, 4→p=800, 5→p=1,000, 6→p=1,200, 7→p=1,400, 8→p=1,600). The y-axis gives the number out of 100 datasets generated with percentage of correct classification ≧80%, ≧70%, ≧60%, ≧50%. FIG. 4 illustrates QDA with direct-resubstitution using MPLS components and PCs. Each row (of plots) correspond to percentage correct classification ≧80%, ≧70%, ≧60%, ≧50%. Each column is the percentage of total predictor variation accounted for by three PCs, ave ($\lambda$,3). The x-axis is the number of variables p (1→p=100, 2→p=300, 3→p=500, 4→p=800, 5→p=1,000, 6→p=1,200, 7→p=1,400, 8→p=1,600). The y-axis gives the number out of 100 datasets generated with percentage of correct classification ≧80%, ≧70%, ≧60%, ≧50%. As expected, QDA with direct resubstitution did better than QDA using cross-validation. For a given real dataset, direct resubstitution in QDA gives inflated level of correct classification and a better indicator is to use cross-validation (Lachenbruch and Mickey, 1968).

Figure 5:
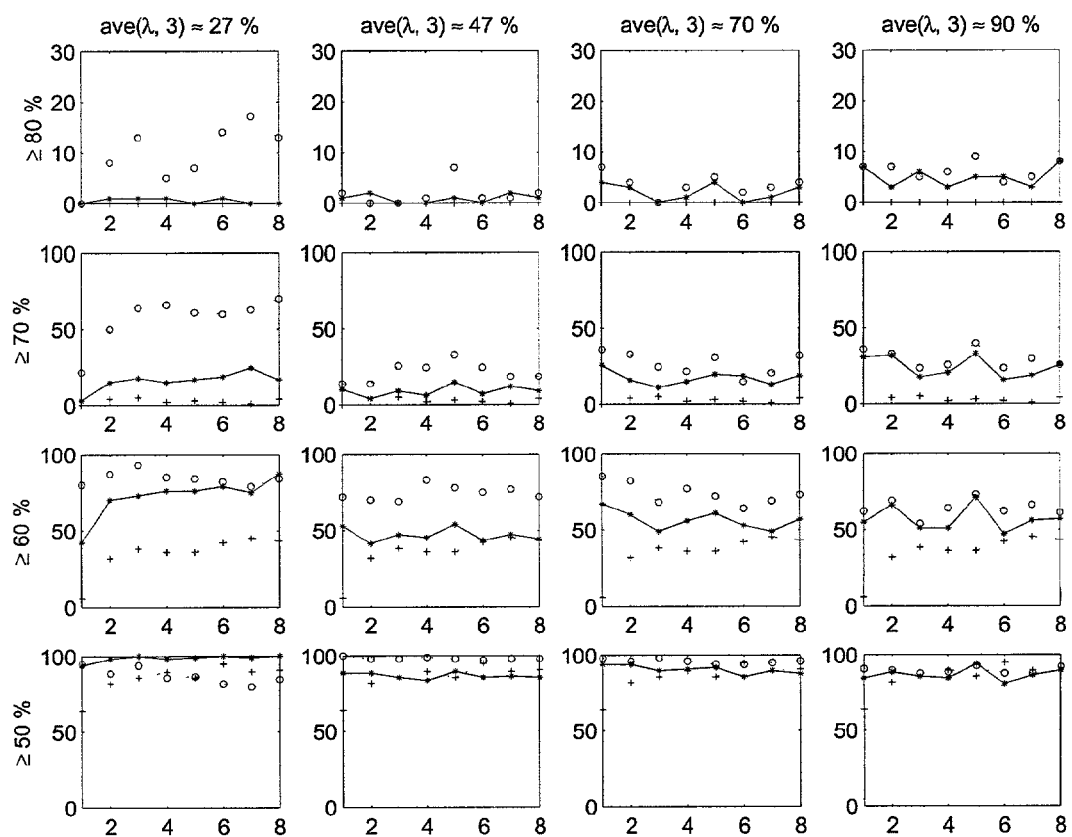
FIG. 5: MPLS components in PD, QDA-direct resubstitution and QDA-CV.

For direct comparison of the performance of MPLS components under the 3 different classification methods, we re-plotted only the MPLS components using (1) PD, (2) QDA-direct resubstitution, and (3) QDA leave-out-one CV in FIG. 5. FIG. 5 illustrates MPLS components in PD (•o•), QDA-direct-resubstitution (-*-), and QDA-CV (-+-). The Figure compares the percentage of correct classification using PD and QDA (direct-resubstitution, and leave-out-one CV) with MPLS components. Each row (of plots) correspond to percentage correct classification ≧80%, ≧70%, ≧60%, ≧50%. Each column is the percentage of total predictor variation accounted for by three PCs, ave ($\lambda$,3). The x-axis is the number of variables p (1→p=100, 2→p=300, 3→p=500, 4→p=800, 5→p=1,000, 6→p=1,200, 7→p=1,400, 8→p=1,600). The y-axis gives the number out of 100 datasets generated with percentage of correct classification ≧80%, ≧70%, ≧60%, ≧50%.. PD performed better than QDA generally, but not always. In a few instances QDA with MPLS components outperformed PD or at least was well. This consistent with classification results from real data reported here for multi-class as well as for binary classification.

5. Multi-Class Classification Conclusions and Discussions

We have described multi-class cancer classification methods that are extension of the binary classification methods described above. The methodologies utilize dimension reduction methods to handle high dimensional data such as the large number of genes in microarray data. Gene components constructed via MPLS performed well with PD and/or QDA. As in the binary case explored earlier, gene components extracted via PCA did not perform as well. This was confirmed in the application of the methods using PLS, MPLS and PCS to 4 cancer data sets as well as to data generated from the simulation model for gene expression data. Although the methods were applied to data sets with various cancers, the classification methods proposed here are general and can be applied in other classification settings for high dimensional biological data as well, as are suggested in the specification. For example, gene expression data from various stages of a particular cancer may be used to predict, e.g., patient survival, drug sensitivity of the tumor, or other clinical outcomes.

An advantage of the methodologies proposed is that other classification methods can be utilized (other than PD and QDA) after dimension reduction via MPLS. As discussed in the Appendix, numerical methods are needed to obtain the MLE in PD and the existence of the MLE depends on the data configuration. One disadvantage of using PD is when there is quasi-complete separation in the data. As one of ordinary skill is aware, detection of quasi-complete separation is numerically burdensome and classification is usually poor. (See Appendix for details.) Also, inversion problems can be encountered in the Newton-Raphson algorithm when searching for the MLE. One of ordinary skill will readily determine how to make use of alternate classification methods in the event that difficulties are encountered with PD or QDA.

6.0 APPENDIX

6.1. PLS Algorithm

The following PLS algorithm is given in Höskuldsson (1988) and adopted in Garthwaite (1994). For details, see also Helland (1988) and Martens and Naes (1989).

1. FOR k=1 to d set u to first column of $Y_{(k)}$ and DO:
2. w=X'u/(u'u) and scale w to be of unit length.
3. t=Xw.
4. c=Y't/(t't) and scale c to be of unit length.
5. u=Yc and GO TO 6 IF convergence ELSE return to 2.
6. p=X't/(t't).
7. b=u't/(t't).

8. Residual matrices: $X_{(k+1)}=X_{(k)}-tp'$ and $Y_{(k+1)}=Y_{(k)}-btc'$ (with $X_{(1)}=X$, $Y_{(1)}=Y$).

9. END FOR

6.1.1. Likelihood Function for Polychotomous Regression

To obtain the likelihood function for N independent samples $(y_1, x_1), \ldots, (y_N, x_N)$ under the polychotomous regression model we first define some notation. Let $c(x_i; \beta)=\log[1+\Sigma_{r=1}^{G} \exp(g_r(x_i))]$ and rewriting (12) we have $\pi(k|x_i)=\exp[(g_k(x_i) \ldots c(x_i; \beta)]$. Thus, $$\log \pi(k|x_i)=g_k(x_i)-c(x_i; \beta). \qquad (20)$$

Also, for the ith observed response value $y_a$ corresponding to explanatory values $x_i=(x_{i0}, x_i, \ldots, x_{ip})'$ (and $x_{i0}\equiv 1$) let $z'_i=(z_{i0}, z_{i1}, \ldots, z_{iG})$ be the row vector indicating whether $y_i$ is in group $k\epsilon o$. That is $z_{ik}=I(y_i=k)$ where $I(A)$ is the indicator function for A. If Z is the $N\times(G+1)$ matrix consisting of rows $z_i$'s then $$\sum_{k=0}^{G} z_{ik} = 1,$$

(the row sums are one). Using the above notations, the likelihood for N independent samples (ignoring constants) is $$L(\beta) = \prod_{i=1}^{N} [\pi(0|x_i)^{z_{i0}}\pi(1|x_i)^{z_{i1}} \cdots \pi(G|x_i)^{z_{iG}}]. \qquad (21)$$

Hence, the log-likelihood is $$l(\beta) = \sum_{i=1}^{N} [z_{i0}\log\pi(0|x_i) + z_{i1}\log\pi(1|x_i) + \cdots + z_{iG}\log\pi(G|x_i)]. \qquad (22)$$

Using (20) together with $$\sum_{k=0}^{K} z_{ik} = 1$$

for each i; the log-likelihood is $$l(\beta) = \sum_{i=1}^{N} [z_{i1}g_1(x_i) + z_{i2}g_2(x_i) + \cdots + z_{iG}g_G(x_i) - c(x_{ij}\beta)]. \qquad (23)$$

(23)

6.1.2. MLE for Polychotomous Regression Using Newton-Raphson

Estimation of $\beta$ is obtained by maximum likelihood estimation (MLE). Iterative methods such as the Newton-Raphson method can be used to obtain the MLE $\hat{\beta}$. This requires first and second order derivatives of $l(\beta)$. For convenience let $\pi_{ik}=\pi(k|x_i; \beta)$. It is straight forward to obtain $$\frac{\partial \pi_{ik}}{\partial \beta_k} = \pi_{ik}(1-\pi_{ik})x_i \ k=1, \ldots, G \qquad (24, 25)$$

$$\frac{\partial \pi_{ik}}{\partial \beta_l} = -\pi_{ik}\pi_{il}x_i \ k=0, 1, \ldots, G.$$

Thus the derivative of $l(\beta)$ with respect to $\beta_k$ is $$S(\beta_k) = \frac{\partial l(\beta)}{\partial \beta_k} = \sum_{i=1}^{N}\left[z_{ik}x_i + \frac{\partial}{\partial \beta_k}c(x_{ij}\beta)\right]$$

$$= \sum_{i=1}^{N} x_i(z_{ik}-\pi_{ik}) \ k=1, \ldots, G$$

since $-c(x_i; \beta)=\log \pi_{i0}$ and $\partial \log \pi_{i0}/\partial \beta_k=-\pi_{ik}x_i$. The score vector is $$S(\beta) = \begin{bmatrix} S(\beta_j) \\ \vdots \\ S(\beta_G) \end{bmatrix}_{G(p|1)\times 1}. \qquad (26)$$

The $G(p+1)$ squared information matrix $I(\beta)=-E[\partial S(\beta)/\partial \beta']$ requires second order derivatives of $l(\beta)$ and are given below $$\frac{\partial l(\beta)}{\partial \beta_k \partial \beta'_l} = -\sum_{i=1}^{N} x_i\left(\frac{\partial \pi_{ik}}{\partial \beta_l}\right)' = \sum_{i=1}^{N} \pi_{ik}\pi_{il}x_i x'_i \qquad (27, 28)$$

$$\frac{\partial l(\beta)}{\partial \beta_k \partial \beta'_k} = -\sum_{i=1}^{N} x_i\left(\frac{\partial \pi_{ik}}{\partial \beta_k}\right)' = -\sum_{i=1}^{N} \pi_{ik}(1-\pi_{ik})x_i x'_i.$$

The asymptotic covariance matrix of the MLE of $\beta$ is the inverse of $l(\beta)$. For iterative computation of the MLE using the Newton-Raphson method is it more concise to express $I(\beta)$ as follows. Define the following $N\times N$ diagonal matrices, $$W_{kk}=diag\{\pi_{1k}(1-\pi_{1k}), \ldots, \pi_{Nk}(1-\pi_{Nk})\}, k=1, \ldots, G$$

$$W_{kl}=diag\{\pi_{1l}\pi_{1k}, \ldots, \pi_{Nl}\pi_{Nk}\}, l\neq k$$

and letting $I_{kk}(\beta)=X'W_{kk}X$ and $I_{kl}(\beta)=I_{lk}(\beta)=-X'W_{kl}X$, the information matrix can be express as $$I(\beta) = \begin{bmatrix} I_{11}(\beta) & I_{12}(\beta) & \cdots & I_{1G}(\beta) \\ I_{21}(\beta) & I_{22}(\beta) & \cdots & I_{2G}(\beta) \\ \vdots & \vdots & & \vdots \\ I_{G1}(\beta) & I_{G2}(\beta) & \cdots & I_{GG}(\beta) \end{bmatrix}_{G(p+1)\times G(p+1)} \qquad (29)$$

For an initial value $\beta^{(0)}$, the MLE of $\beta$ is obtained iteratively through $\beta^{(t+1)}=\beta^{(t)}+I^{-1}(\beta^{(t)})S(\beta^{(t)})$. If the Newton-Raphson algorithm converges, then the vector of coefficients at convergence is denoted $\hat{\beta}$ and it is the MLE of $\beta$.

6.1.3. Existence of MLE for Polychotomous Regression Model

We briefly describe the conditions for existence of the MLE of $\beta$ in the polychotomous regression model. The reader is referred to Albert and Anderson (1984) for details. Possible data configurations can be categorized into three mutually exclusive and exhaustive groups: (1) complete separation, (2) quasicomplete separation, and (3) overlap. The first two situations lead to parameter estimates often referred to as "infinite parameters." Specifically for (1) there exists a vector 8 which correctly classify all observations to their class, i.e.

$$(\beta_k - \beta_j)'x_i > 0 \quad k,j=0, \ldots, G \ (k \neq j)$$

for all $i \in C_k$, where $C_k$ ($k=0, \ldots, G$) is an index set identifying all samples in class k. Here, the MLE does not exist and the −2log-likelihood decreases to zero. Empirical detection of complete separation is to stop iteration when the probability of correct classification is 1 for all samples. Nearly all model fits with MPLS components reported here are of this type. Quasicomplete separation is when there is a vector $\beta$ such that $$(\beta_k \ldots \beta_j)'x_i \geq 0 \quad k,j=0, \ldots, G \ (k \neq j)$$

for all $i \in C_k$ and the equality holds for at least one (i, k, j) (one sample in each class). Again, the MLE does not exist for this data configuration. Empirical detection is based on monitoring the probability of correct classification approaching one and the dispersion matrix, which is unbounded. This was encountered often with PCs. For the third case, overlap, the MLE exist and is unique.

The foregoing description is intended to illustrate but not limit the invention, the scope of which is defined by the claims. Additional embodiments and variations that do not depart from the invention but rather are within the scope of the invention will be apparent to those skilled in the art in view of the description provided herein. All references cited within the specification, including patents, patent applications, and scientific publications are hereby incorporated by reference in their entirety for all purposes.

REFERENCES

1. Albert, A. and Anderson, J. A. (1984), "On the Existence of Maximum Likelihood Estimates in Logistic Models," *Biometrika*, 71, 1–10.
2. Alizadeh, A. A., Eisen, M. B., Davis, R. E., Ma, C., Lossos, I. S., Rosenwald, A., Broldrick, J. C., Sabet, H. Tran, T., Yu, X., Powell, J. I., Yang, L., Marti, G. E., Moore, T., Hudson, J. Jr., Lu, L., Lewis, D. B., Tibshirani, R., Sherlock, G., Chan, W. C., Greiner, T. C., Weisenburger, D. D., Armitage, J. O., Warrke, R., Levy, R., Wilson, W., Grever, M. R., Byrd, J. C., Botstein, D., Brown, P. O., and Staudt, L. M. (2000), "Distinct Types of Diffuse Large B-Cell Lymphoma Identified by Gene Expression Profiling," *Nature*, 403, 503–511.
3. Alon, U., Barkai, N., Notterman, D. A., Gish, K., Ybarra, S., Mack, D., and Levine, A. J. (1999), "Broad Patterns of Gene Expression Revealed by Clustering Analysis of Tumor and Normal Colon Tissues Probed by Oligonucleotide Arrays," *Proceedings of the National Academy of Sciences*, 96, 6745–6750.
4. Bittner, M., Meltzer, P., Chen, Y., Jiang, Y., Seftor, E., Hendrix, M., Radmacher, M., Simon, R., Yakhini, Z., Ben-Dor, A., Sampas, N., Dougherty, E., Wang, E., Marincola, F., Gooden, C., Lueders, J., Glatfelter, A., Pollock, P., Carpten, J., Gillanders, E., Leja, D., Dietrich K., Beaudry, C., Berens, M., Alberts, D., Sondak, V., Hayward, N., and Trent, J. (2000), "Molecular Classification of Cutaneous Malignant Melanoma by Gene Expression Profiling," *Nature*, 406, 536–540.
5. Catteau A., Harris W. H., Xu C. F. and Soloman E. (1999), "Methylation of the BRCA1 Promoter Region in Sporadic Breast Cancer: Correlation with Disease Characteristics," *Oncogene*, 18, 1957–1965.
6. Cox, D. R. (1972), "Regression Models and Life-Tables" (with discussion), *Journal of the Royal Statistical Society*, Series B, 34, 187–220.
7. de Jong, S. (1993), "SIMPLS: An Alternative Approach to Partial Least Squares Regression," *Chemometrics and Intelligent Laboratory Systems*, 18, 251–263.
8. DeRisi, J., Penland, L., Brown, P.O., Bittner, M. L., Meltzer, P. S., Ray, M., Chen, Y., Su, Y. A., and Trent, J. M. (1996), "Use of cDNA Microarray to Analyse Gene Expression Patterns in Human Cancer," *Nature Genetics*, 14, 457–460.
9. Esteller, M., Silva J. M., Domingquez G., Bonilla, F., Matias-Guiu, X., Lerma, E., Bussaglia, E., Prat, J., Harkes, I. C., Repasky, E. A., Gabrielson, E., Schutte, M., Baylin, S. B., Herman, J. G. (2000), "Promoter Hypermethylation and BRCA1 Inactivation in Sporadic Breast and Ovarian Tumors," *Journal of the National Cancer Institute*, 92, 564–569.
10. Flury, B. (1997), *A First Course in Plultivariate Analysis*. Springer-Verlag, New York.
11. Frank, I. E., and Friedman, J. H. (1993), "A Statistical View of Some Chemometrics Regression Tools" (with discussion), *Technometrics*, 35, 109–148.
12. Furey, T. S., Cristianini, N., Duffy, N., Bednarski, D. W., Schummer, M., Haussler, D. (2000), "Support Vector Machine Classification and Validation of Cancer Tissue Samples Using Microarray Expression Data," *Bioinformatics*, 16, 906–914.
13. Garthwaite, P. H. (1994), "An Interpretation of Partial Least Squares," *Journal of the American Statistical Association*, 89, 122–127.
14. Geladi, P., and Kowalski, B. R. (1986), "Partial Least Squares Regression: A Tutorial," *Analytica Chimica Acta*, 185, 1–17.
15. Golub, T. R., Slonim, D. K., Tamayo, P., Huard, C., Gaasenbeek, M., Mesirov, P., Coller, H., Loh, M. L., Downing, J. R., Caligiuri, M. A., Bloomfield, C. D., and Lander, E. S. (1999), "Molecular Classification of Cancer: Class Discovery and Class Prediction by Gene Expression Monitoring," *Science*, 286, 531–537.
16. Hedenfalk, I., Duggan, D., Chen, Y., Radmacher, M., Bittner, M., Simon, R., Meltzer, P., Gusterson, B., Esteller, M., Kallioniemi, O., Wilfond, B., Borg, A., Trent, J., et al. (2001), "Gene-Expression Profiles in Hereditary Breast Cancer," *The New England Journal of Medicine*, 344 539–548.
17. Helland, I. S. (1988), "On the Structure of Partial Least Squares," *Communications in Statistics-Simulation and Computation*, 17, 581–607.
18. Helland, S., and Almoy, T. (1994), "Comparison of Prediction Methods When Only a Few Components are Relevant," *Journal of the American Statistical Association*, 89, 583–591.
19. Hoskuldsson, A. (1988), "PLS Regression Methods," *Journal of Chemometrics*, 2,211228.
20. Hosmer, D. W., and Lemeshow, S. (1989), *Applied Logistic Regression*. John Wiley & Sons, New York.

21. Johannsson O. T., Idvall, I., Anderson, C., Borg, A., Barkarbttir, V., Egilsson, V. and Olsson, S. (1997), "Tumor Biological Features of BRCA1-induced Breast and Ovarian Cancer," *Eur. J. Cancer,* 33, 362–371.
22. Johnson, R. A. and Wichern, D. W. (1992), *Applied Multivariate Analysis.* PrenticeHall, New Jersey, 4th edition.
23. Jolliffe, I. T. (1986), *Principal Component Analysis.* Springer-Verlag, New York.
24. Kaplan, E. L. and Meier, P. (1958), "Nonparametric Estimation from Incomplete Observations," *Journal of the American Statistical Association,* 53, 457–481.
25. Karp, S. E., Tonin, P.N., Begin L. R., et al. (1997), "Influence of BRCA1 Mutations on Nuclear Grade and Estrogen Receptor Status of Breast Carcinoma in Ashkenazi Jewish Women," *Cancer,* 80, 435–441.
26. Kooperberg, C., Bose, S., and Stone, C. J. (1997), "Polychotomous Regression," *Journal of the American Statistical Association,* 92, 117–127.
27. Lachenbruch, P. A., and Mickey, M. R. (1968), "Estimation of Error Rates in Discriminant Analysis," *Technometrics,* 10, 1–11.
28. Lockhart, D., Dong, H., Byrne, M., Follettie, M., Gallo, M., Chee, M., Mittmann, M., Wang, C., Kobayashi, M., Horton, H., and Brown, E. (1996), "Expression Monitoring by Hybridization to High-Density Oligonucleotide Arrays, *Nature Biotechnol.,* 14, 1675–1680.
29. Loman, N. Johannsson, O., Bendahl, P. O., Borg, A., et al. (1998), "Steroid Receptors in Hereditary Breast Carcinomas Associated with BRCA1 and BRCA2 Mutations or Unknown Susceptibility Genes," *Cancer,* 83, 310–409.
30. Lorber, A., Wangen, L. E., and Kowalski, B. R. (1987), "A Theoretical Foundation for the PLS Algorithm," *Journal of Chemometrics,* 1, 19–31.
31. Mardia, K. V., Kent, J. T., and Bibby, J. M. (1979), *Multivariate Analysis.* Academic Press, London.
32. Martens, H. and Naes, T. (1989), *Multivariate Calibration.* John Wiley & Sons, New York.
33. Massey, W. F. (1965), "Principal Components Regression in Exploratory Statistical Research," *Journal of the American Statistical Association* 60, 234–246.
34. McCullagh, P. and Nelder, J. A. (1989), *Generalized Linear Models,* 2nd Ed. Chapman and Hall, London.
35. Nguyen, D. V. and Rocke, D. M. (2000), "Classification in High Dimension with Application to DNA Microarray Data," manuscript.
36. Nguyen, D. V. and Rocke, D. M. (2001), "Tumor Classification by Partial Least Squares Using Microarray Gene Expression Data," to appear in *Bioinformatics.*
37. Perou, C. M., Jeffrey, S. S., van de Rijn, M., Rees, C. A., Eisen, M. B., Ross, D. T., Pergamenschikov, A., Williams, C. F., Zhu, S. X., Lee, J. C. F., Lashkari, D., Shalon, D., Brown, P. O., and Botstein, D. (1999), "Distinctive Gene Expression Patterns in Human Mammary Epithelial Cells and Breast Cancer," *Proceedings of the National Academy of Sciences, USA,* 96, 9112–9217.
38. Perou, C. M., Sorlie, T., Eisen, M. B., van de Rijn, M., Jeffrey, S. S., Rees, C. A., Pollack, J. R., Ross, D. T., Johnsen, H., Akslen, L. A., Fluge, O., Pergamenschikov, A., Williams, C., Zhu, S. X., Lonning, P. E., Borresen-Dale, A., Brown, P. O., and Botstein, D. (2000), "Molecular Portrait of Human Breast Tumors," *Nature,* 406, 747752.
39. Phatak, A., and Reilly, P. M., and Penlidis, A. (1992), "The Geometry of 2-Block Partial Least Squares," *Communications in Statistics-Theory and Methods,* 21, 15171553.
40. Press, S. J. (1982), *Applied Multivariate Analysis: Using Bayesian and Frequentist Methods of Inference.* Robert E. Krieger Publishing Company Inc., Malabar, Fl., 2nd edition.
41. Ross, D. T., Scherf, U., Eisen, M. B,. Perou, C. M., Rees, C., Spellman, P., Iyer, V., Jeffrey, S. S., Rijin, M. V., Waltham, M., Pergamenschikov, A., Lee, J., Lashkari, D., Shalon, D., Myers, T. G., Weinstein, J. N., Botstein, D., and Brown, P. O. (2000), "Systematic Variation in Gene Expression Patterns in Human Cancer Cell Lines," *Nature Genetics,* 24, 227–235.
42. Scherf, U., Ross, D. T., Waltham, M., Smith, L. H., Lee, J. K., Tanabe, L., Kohn, K. W., Reinhold, W. C., Myers, T. G., Andrews, D. T., Scudiero, D. A., Eisen, M. B., Sausville, E. A., Pommier, Y., Botstein, D., Brown, P. O. and Weinstein, J. N. (2000), "A Gene Expression Database for the Molecular Pharmacology of Cancer," *Nature Genetics,* 24, 236–244.
43. Stone, M., and Brooks, R. J. (1990), "Continuum Regression: Cross-validated Sequentially Constructed Prediction Embracing Ordinary Least Squares, Partial Least Squares, and Principal Components Regression" (with discussion), *Journal of the Royal Statistical Society,* Series B, 52, 237–269.
44. Vapnik, V. N. (2000), *The Nature of Statistical Learning Theory,* 2nd Ed. SpringerVerlag, New York.
45. Verhoog, L. C., Brekelmans, C. T., Seynaeve, C., et al. (1998), "Survival and Tumor Characteristics of Breast-Cancer Patients with Germline Mutations of BRCA1," *Lancet,* 351, 316–321.

We claim:

1. A method of classifying a biological sample, comprising:

calculating K partial least squares components from an N×p input data set, wherein N is a number of samples in the data set, p is a number of predictors observed for the N samples, wherein K<p, and wherein said input data set has for each of the N samples an associated response variable, y, that identifies one of G groups to which each of the N samples belongs, using said K partial least squares components to calculate a set of classification equations, and applying said classification equations to a data set obtained from a biological sample to predict which of said G groups the sample belongs to and thereby classify the sample, wherein said input data set and said data set obtained from a biological sample comprise gene expression measurements.

2. The method of claim 1, wherein said partial least squares components are modified using singular value decomposition prior to calculating said set of classification equations.

3. The method of claim 1, wherein said partial least squares components are modified using linear combinations of univariate logistic regression prior to calculating said set of classification equations.

4. The method of claim 1, wherein said input data are normalized to have a mean of zero and a standard deviation of one.

5. The method of claim 1, wherein said input data set and said data set obtained from a biological sample comprise ratios between a reference and a test measurement.

6. The method of claim 1, wherein G=2, said response variable, y, is binary, and said binary response variable, y, is used for calculating said K partial least squares components.

7. The method of claim 6, wherein said classification equations are calculated using logistic regression.

8. The method of claim 6, wherein said classification equations are calculated using quadratic discriminant analysis.

9. The method of claim 6, wherein said classification equations are calculated using linear discriminant analysis.

10. The method of claim 6, wherein said G groups are tumor and normal groups.

11. The method of claim 1, further comprising determining an estimated conditional class probability of the prediction.

12. The method of claim 11, wherein G is an integer greater than 2, said method further comprising creating (G+1) indicator variables and using multivariate partial least squares on the vector response of the (G+1) indicator variables to calculate said K partial least squares components.

13. The method of claim 12, wherein said G groups include different tumor types.

14. The method of claim 12, wherein said G groups include predicted survival times.

15. The method of claim 12, wherein said G groups include different cellular reactions to drug therapy.

16. The method of claim 12, wherein said classification equations are calculated using polychotomous logistic regression.

17. The method of claim 12, wherein said classification equations are calculated using quadratic discriminant analysis.

18. The method of claim 12, wherein the classification equations are calculated using liner discriminant analysis.

* * * * *

UNITED STATES PATENT AND TRADEMARK OFFICE
CERTIFICATE OF CORRECTION

PATENT NO. : 7,062,384 B2  
APPLICATION NO. : 09/957100  
DATED : June 13, 2006  
INVENTOR(S) : David M. Rocke and Danh V. Nguyen Page 1 of 1

It is certified that error appears in the above-identified patent and that said Letters Patent is hereby corrected as shown below:

Claim 18, Column 40, Line 14, replace "liner" with --linear--.

Signed and Sealed this

Eighth Day of August, 2006

JON W. DUDAS  
*Director of the United States Patent and Trademark Office*